(12) United States Patent
Kudo et al.

(10) Patent No.: US 8,093,449 B2
(45) Date of Patent: Jan. 10, 2012

(54) ABSORBENT ARTICLE

(75) Inventors: Jun Kudo, Ehime (JP); Hideyuki Kinoshita, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 97 days.

(21) Appl. No.: 12/444,672

(22) PCT Filed: Nov. 16, 2007

(86) PCT No.: PCT/JP2007/072282
§ 371 (c)(1),
(2), (4) Date: May 12, 2009

(87) PCT Pub. No.: WO2008/059957
PCT Pub. Date: May 22, 2008

(65) Prior Publication Data
US 2010/0010463 A1    Jan. 14, 2010

(30) Foreign Application Priority Data

Nov. 17, 2006    (JP) .................................. 2006-311224

(51) Int. Cl.
*A61F 13/15*    (2006.01)
*A61F 13/20*    (2006.01)
(52) U.S. Cl. .................................. 604/378; 604/385.01
(58) Field of Classification Search .................. 604/378, 604/385.101, 385.11, 385.16, 385.17, 386–387
See application file for complete search history.

(56) References Cited

U.S. PATENT DOCUMENTS

H1614 H * 11/1996 Mayer et al. ............. 604/385.23

(Continued)

FOREIGN PATENT DOCUMENTS

JP    5-33721 U    5/1993
(Continued)

OTHER PUBLICATIONS

International Search Report of Application No. PCT/JP2007/072282 mailed Feb. 19, 2008.

*Primary Examiner* — Michele M Kidwell
(74) *Attorney, Agent, or Firm* — Lowe, Hauptman, Ham & Berner, LLP

(57)    ABSTRACT

The invention includes an absorbent article 1 in which an undergarment 90 can be prevented from getting dirty with fluid that has been absorbed by an absorbent body 20, without a decrease in the amount of fluid that can be absorbed.

The absorbent article 1 that is worn on a human body and used includes an absorbent body 20 having a fluid-absorbent member 22 for absorbing fluid, and having a longitudinal direction, a width direction, and a thickness direction, and a main body section 10 whose face on the side of the human body is overlapped with the absorbent body 20 in the thickness direction, one end section 20a in the longitudinal direction of the absorbent body 20 being fixed to the main body section 10, the absorbent body 20 having a portion that is closer to the main body section 10 than the fluid-absorbent member 22 in the thickness direction and a portion that is closer to the human body than the fluid-absorbent member 22, wherein the portion closer to the main body section 10, in another end section 20b in the longitudinal direction of the absorbent body 20, is covered with a fluid-impermeable layer 50, and the portion closer to the human body, in the other end section 20b, has a portion in which the fluid-impermeable layer 50 is not included.

12 Claims, 22 Drawing Sheets

U.S. PATENT DOCUMENTS

| | | | |
|---|---|---|---|
| 5,827,261 A * | 10/1998 | Osborn et al. | 604/387 |
| 6,280,427 B1 * | 8/2001 | Maggiulli | 604/385.01 |
| 6,652,498 B1 | 11/2003 | Glasgow et al. | |
| 6,802,833 B2 * | 10/2004 | Kudo | 604/385.02 |
| 6,802,932 B2 * | 10/2004 | Kudo et al. | 156/322 |
| 7,078,583 B2 * | 7/2006 | Kudo et al. | 604/380 |
| 7,628,777 B2 * | 12/2009 | Kondo et al. | 604/385.101 |
| 2003/0187417 A1 * | 10/2003 | Kudo et al. | 604/379 |
| 2003/0187418 A1 * | 10/2003 | Kudo et al. | 604/380 |

FOREIGN PATENT DOCUMENTS

| | | |
|---|---|---|
| JP | 10-504486 A | 5/1998 |
| JP | 2001-314439 A | 11/2001 |
| JP | 2002-159534 A | 6/2002 |
| WO | 96/05790 A1 | 2/1996 |

* cited by examiner

A-A CROSS SECTION

B-B CROSS SECTION

C-C CROSS SECTION

D-D CROSS SECTION

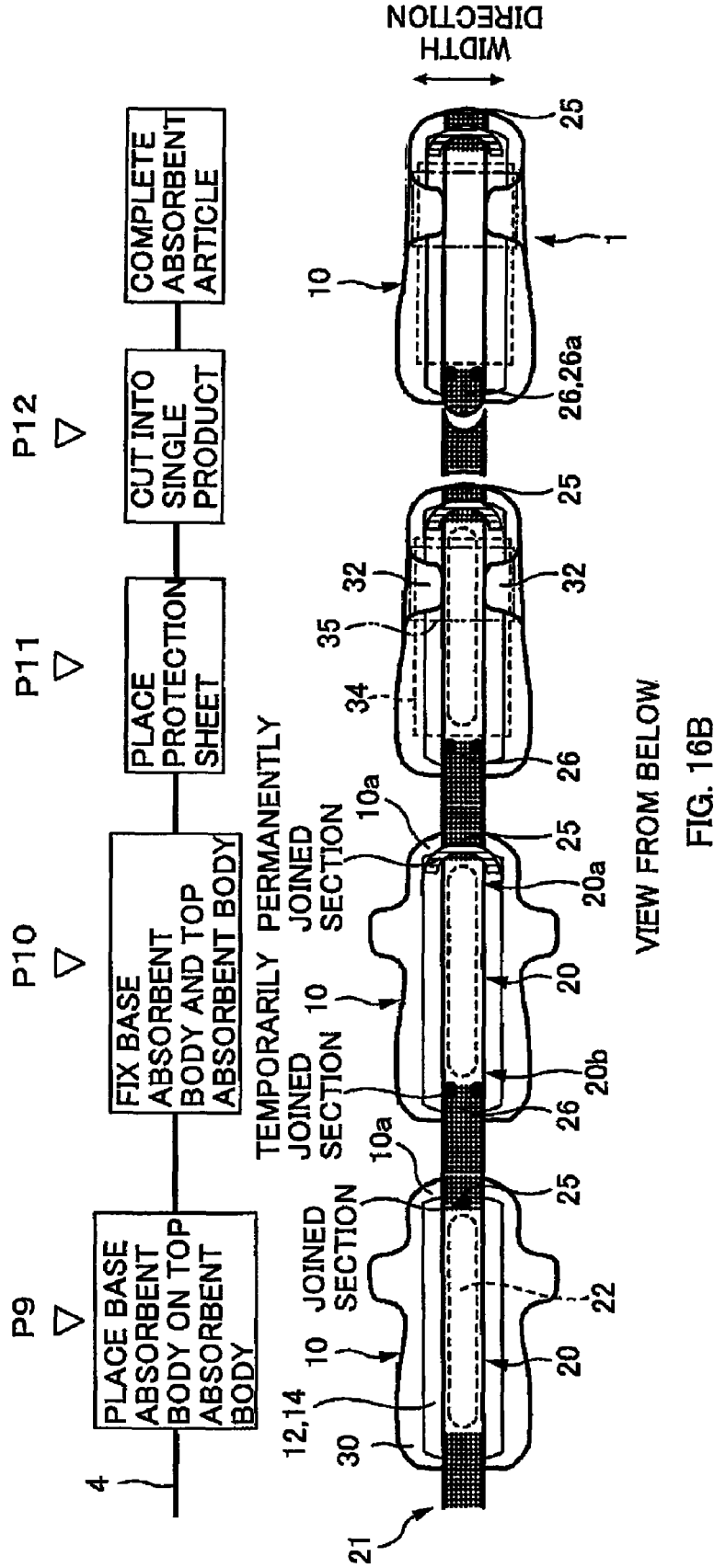

ABSORBENT ARTICLE

RELATED APPLICATIONS

The present application is based on International Application Number PCT/JP2007/072282 filed Nov. 16, 2007, and claims priority from Japanese Application Number 2006-311224, filed Nov. 17, 2006, the disclosures of which are hereby incorporated by reference herein in their entirety.

TECHNICAL FIELD

The present invention relates to an absorbent article.

BACKGROUND ART

As an example of an absorbent article that absorbs certain fluid such as menstrual blood, there is an absorbent article including (1) a main body section that is to be fixed to an undergarment, and (2) an absorbent body that has a fluid-absorbent member such as fluid-absorbent pulverized pulp or the like, which is overlapped with the main body section, and that has a front end section in the longitudinal direction fixed to the main body section and a rear end section separable from the main body section (refer to Patent Document 1, for example).

And at the time of use, the main body section is fixed to the inner face (that is, the face on the side of a human body) of the undergarment while the longitudinal direction of the absorbent body is set along the front-and-rear direction of the human body. After that, in a state where the undergarment is worn, the rear end section of the absorbent body is pulled up so that the absorbent body is placed in the groove of the buttocks and the like. Accordingly, the absorbent body is sandwiched and fixed in the groove of the buttocks and the like (refer to JP-A-2002-159534).

DISCLOSURE OF INVENTION

Problems to be Solved by the Invention

However, the rear end section of the absorbent body may project rearward from the external outline of the main body section, depending on how the rear end section is pulled up or the length of the absorbent body relative to the main body section, for example. And in such a case, an outer face on the side of the main body section, of the rear end section projecting rearward from the external outline, is brought into direct contact with an undergarment. In such a situation, if fluid that has been absorbed by the fluid-absorbent member oozes out to the outer face of the absorbent body, the undergarment gets dirty with the fluid.

With respect to this point, in the absorbent article according to Patent Document 1 mentioned above, a watertight section is provided in the area near the rear end section of the absorbent body, and thus movement of fluid toward the rear end section side over the watertight section is blocked.

However, with the function of the watertight section to block movement of fluid to the rear end section side, the interior of the watertight section cannot be filled with the fluid-absorbent member. More specifically, in the absorbent article of Patent Document 1, the watertight section serves as an area having no fluid-absorbent member disposed in the longitudinal direction. As a result, in a case where this watertight section is disposed, there will be a problem that the amount of fluid that can be absorbed by the absorbent body decreases by the volume of the watertight section.

The present invention was made in view of the foregoing conventional problem, and it is an advantage thereof to provide an absorbent article in which an undergarment can be prevented from getting dirty with fluid that has been absorbed by an absorbent body, without a decrease in the amount of fluid that can be absorbed.

Means for Solving the Problems

A main aspect of the invention for realizing the above-described advantage is an absorbent article that is worn on a human body and used,
including
an absorbent body having a fluid-absorbent member for absorbing fluid, and having a longitudinal direction, a width direction, and a thickness direction, and
a main body section whose face on the side of the human body is overlapped with the absorbent body in the thickness direction,
one end section in the longitudinal direction of the absorbent body being fixed to the main body section,
the absorbent body having a portion that is closer to the main body section than the fluid-absorbent member in the thickness direction and a portion that is closer to the human body than the fluid-absorbent member,
wherein the portion closer to the main body section, in another end section in the longitudinal direction of the absorbent body, is covered with a fluid-impermeable layer, and
the portion closer to the human body, in the other end section, has a portion in which the fluid-impermeable layer is not included.

Features of the present invention other than the above will be made clear in the descriptions of the present specification and the accompanying drawings.

Effects of the Invention

According to the present invention, it is possible to provide an absorbent article in which an undergarment can be prevented from getting dirty with fluid that has been absorbed by an absorbent body, without a decrease in the amount of fluid that can be absorbed.

BRIEF DESCRIPTION OF DRAWINGS

FIG. 16B is an explanatory view of a "base absorbent body combination operation" in FIG. 15.

LIST OF REFERENCE NUMERALS

Figure 1:
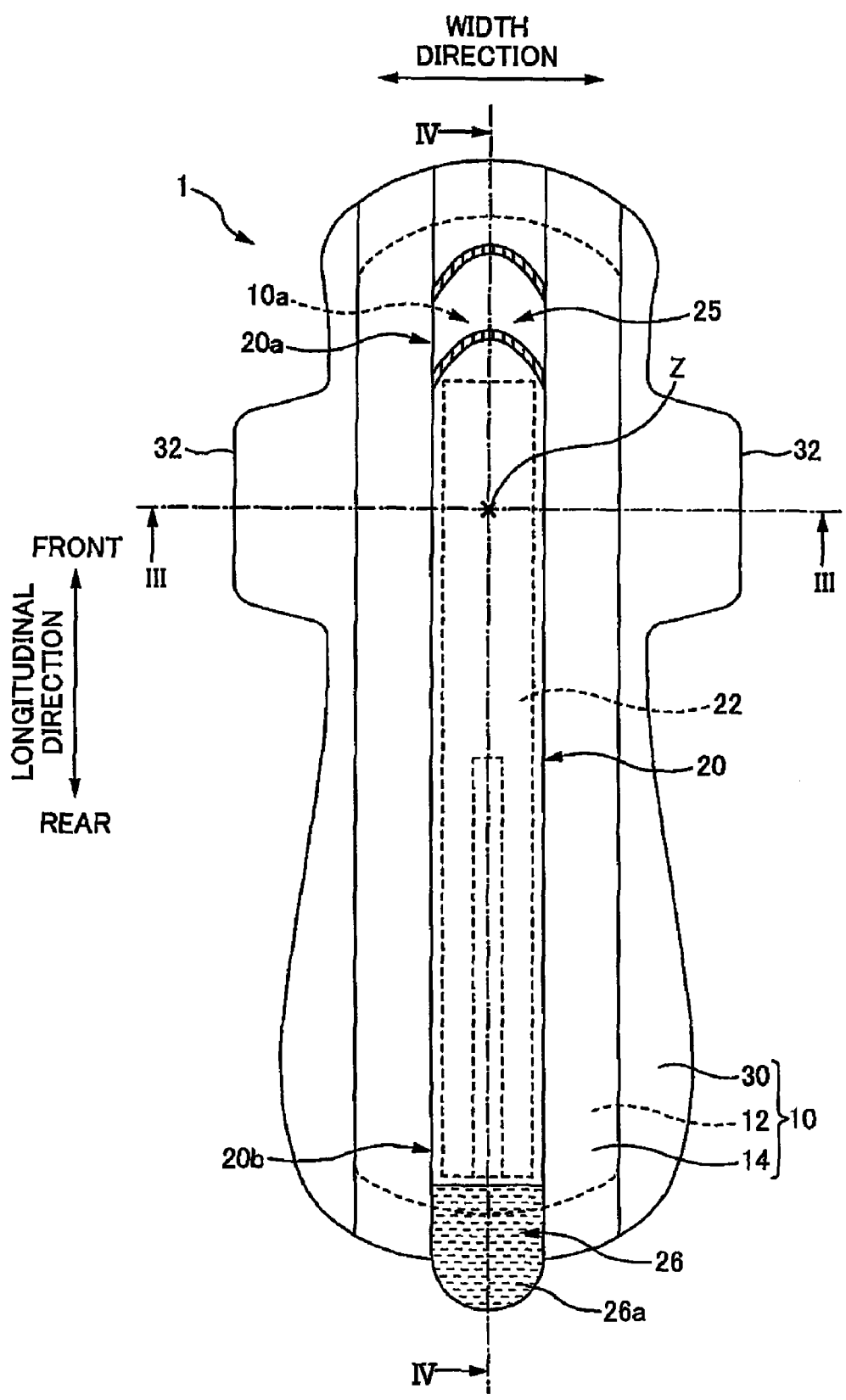
FIG. 1 is a plan view showing the surface side of an absorbent article 1 in an unfolded state.

1 . . . absorbent article, 1a . . . front end section, 1b . . . rear end section, 3 . . . transporting apparatus, 4 . . . transporting apparatus, 10 . . . base absorbent body (main body section), 10a . . . front end section, 10b . . . rear end section, 10e . . . rear edge, 12 . . . absorbent body base material, 12a . . . pulverized pulp, 14 . . . surface sheet, 20 . . . top absorbent body (absorbent body), 20a . . . front end section (one end section), 20b . . . rear end section (the other end section), 20e . . . rear edge, 21 . . . continuous body of top absorbent bodies, 22 . . . pulverized pulp (fluid-absorbent member), 22 . . . surface, 22b . . . back face, 22c . . . side face, 22d . . . rear end section, 22e . . . rear edge, 22f . . . thin wall section, 22g . . . corner section, 23 . . . intermediate sheet, 23b . . . rear end section, 24 . . . shape retaining sheet, 24a . . . shape retaining sheet, 24b . . . shape retaining sheet, 24c . . . section, 24d . . . section, 24e . . . end section, 25 . . . front sealed section, 26 . . . rear sealed section, 26a . . . pick-up section, 26b . . . section, 27 . . . hook member, 30 . . . back face sheet, 30a . . . front end section, 30b . . . rear end section, 30c . . . back face, 30e . . . rear edge, 31 . . . undergarment fixation adhesive, 32 . . . wing section, 33 . . . undergarment fixation adhesive, 34 . . . protection sheet, 35 . . . protection sheet, 36 . . . wrapping sheet, 36c . . . edge section, 38 . . . lead tape, 50 . . . fluid-impermeable layer, 51 leakage prevention sheet (fluid-impermeable sheet), 90 . . . undergarment, Z . . . position assumed to abut against the human bodily discharge opening

BEST MODE FOR CARRYING OUT THE INVENTION

At least the following matters will be made clear in the description of the present specification and the accompanying drawings.

The invention is directed to an absorbent article that is worn on a human body and used,
comprising
an absorbent body having a fluid-absorbent member for absorbing fluid, and having a longitudinal direction, a width direction, and a thickness direction, and
a main body section whose face on the side of the human body is overlapped with the absorbent body in the thickness direction,
one end section in the longitudinal direction of the absorbent body being fixed to the main body section,
the absorbent body having a portion that is closer to the main body section than the fluid-absorbent member in the thickness direction and a portion that is closer to the human body than the fluid-absorbent member,
wherein the portion closer to the main body section, in another end section in the longitudinal direction of the absorbent body, is covered with a fluid-impermeable layer, and
the portion closer to the human body, in the other end section, has a portion in which the fluid-impermeable layer is not included.

With such an absorbent article, an undergarment can be effectively prevented from getting dirty with fluid that has been absorbed by the fluid-absorbent member of the absorbent body. More specifically, the other end section of the absorbent body can be separated from the main body section, and thus the other end section may project out from the main body section depending on how the absorbent article is worn on the human body, for example. And in such a case, in the other end section of the absorbent body, an outer face on the side of the main body section is brought into contact with an undergarment. However, here, with the above-described absorbent article, a fluid-impermeable layer is provided in the other end section so as to cover a portion that is closer to the main body section than the fluid-absorbent member. Thus, seepage of fluid from the fluid-absorbent member to the outer face on the side of main body section, in the other end section, is suppressed by the fluid-impermeable layer. As a result, a portion of the undergarment positioned on the side of main body section can be effectively prevented from getting dirty.

Furthermore, the fluid-impermeable layer is included so that it covers a portion that is closer to the main body section than the fluid-absorbent member in the absorbent body. Thus, there is no need to include an area with no fluid-absorbent member disposed regarding the longitudinal direction. Accordingly, the fluid-absorbent member in an amount corresponding to the total length of the absorbent body can be maintained, and as the result the amount of fluid that can be absorbed by the absorbent body does not have to decrease in accordance with formation of the fluid-impermeable layer.

Moreover, the portion that is closer to the human body than the fluid-absorbent member (the portion that is on a farther side from the main body section than the fluid-absorbent member) includes a portion in which the fluid-impermeable layer is not included. Thus, fluid that has been discharged from the human body, which is generally positioned on the human body side (positioned at a farther side from the main body section), can be directly absorbed also in the other end section.

Furthermore, in the other end section, the portion of the human body side (the portion of the side that is a farther side from the main body section) is brought into contact with the human body. However, this portion is not included with the fluid-impermeable layer. Thus, the fluid-impermeable layer is not brought into contact with the human body. Accordingly, in the case of choosing the material of the fluid-impermeable layer, there is no need to consider texture, therefore the degree of freedom in choosing the material of the fluid-impermeable layer increases.

In such an absorbent article, it is desirable that in an unfolded state in which the main body section and the absorbent body, which have been overlapped, are unfolded flat, the other end section of the absorbent body is projected outward from an external outline of the main body section, and in the unfolded state, the fluid-impermeable layer is extended, in the longitudinal direction in the other end section, at least from a position opposing the external outline of the main body section to a position of an end section of the fluid-absorbent member.

With such an absorbent article, the fluid-impermeable layer is extended, at least from a position opposing the external outline of the main body section in the other end section to a position of the end section of the fluid-absorbent member in the other end section. Therefore, an undergarment can be effectively prevented from getting dirty with a portion of the absorbent body projected outward from the external outline.

In such an absorbent article, it is desirable that the fluid-impermeable layer is included spanning the external outline in the longitudinal direction and spanning the end section of the fluid-absorbent member in the other end section in the longitudinal direction.

With such an absorbent article, the fluid-impermeable layer is included spanning the external outline in the longitudinal direction and spanning the end section of the fluid-absorbent member in the other section in the longitudinal direction. Thus, an undergarment can be more effectively prevented from getting dirty with a portion of the absorbent body projected outward from the external outline.

In such an absorbent article, it is desirable that the fluid-impermeable layer is included only in the other end section and its vicinity on the absorbent body.

With such an absorbent article, in the absorbent body, the fluid-impermeable layer is not included in sections other than the other end section and its vicinity. Thus, a long area in the longitudinal direction can be secured in which fluid that has been discharged from the human body can be directly absorbed. Accordingly, the absorbent article having a good fluid-absorbing ability can be formed.

Furthermore, according to the above-described configuration, in sections other than the other end section and its vicinity, the fluid-impermeable layer is not formed on the portion that is closer to the main body section than the fluid-absorbent member in the thickness direction. Therefore, even in the case where the amount of fluid actually absorbed by the fluid-absorbent member of the absorbent body exceeds the amount of fluid that can be absorbed, excess fluid that exceeds the amount of fluid that can be absorbed penetrates into the main body section through the portion of the absorbent body that is on the main body section side, that is, the excessive fluid can be absorbed by the main body section. Accordingly, an absorbent article can be configured that can absorb a large amount of fluid.

In such an absorbent article, it is desirable that the absorbent body has a fluid-permeable shape retaining sheet for retaining the fluid-absorbent member in the shape of a long article that is long in the longitudinal direction by wrapping around the fluid-absorbent member, and a fluid-impermeable sheet interposed between the fluid-absorbent member and the shape retaining sheet forms the fluid-impermeable layer.

With such an absorbent article, it is the shape retaining sheet that can be brought into contact with the user's body, and the fluid-impermeable sheet is not brought into contact with the body. Thus, in the case of choosing the material of the fluid-impermeable sheet, there is no need to consider texture, and therefore the degree of freedom in choosing the material of the fluid-impermeable layer increases.

In such an absorbent article, it is desirable that the fluid-impermeable sheet is attached to the shape retaining sheet.

With such an absorbent article, the absorbent body that includes the fluid-impermeable layer is formed, by attaching the fluid-impermeable sheet to the shape retaining sheet, and after that wrapping the fluid-absorbent member in the shape retaining sheet. Thus, it is possible to easily form the absorbent body that includes the fluid-impermeable layer. As a result, the absorbent article can be mass-produced in an excellent manner.

In such an absorbent article, it is desirable that the color of an outer face of the absorbent body is white, and the color of the fluid-impermeable layer is a color other than white and red.

With such an absorbent article, the color of fluid that has been absorbed by the fluid-absorbent member, which is the color that is visually confirmed through the fluid-impermeable layer, is a color other than red. Thus, a visual relief can be given to the user.

In such an absorbent article, it is desirable that the interior of the absorbent body is filled with the fluid-absorbent member continuously from the one end section to the other end section in the longitudinal direction.

With such an absorbent article, the fluid-absorbent member is present substantially throughout the total length in the longitudinal direction inside the absorbent body. Thus, the absorbent article is included with a good fluid-absorbing ability.

In such an absorbent article, the main body section may be in a shape that is long in the longitudinal direction, and at the same time, in a shape wider than the absorbent body in a width direction that is perpendicular to the longitudinal direction, the absorbent body may be disposed by being positioned in the middle in the width direction while the longitudinal direction of the absorbent body is matched to the longitudinal direction of the main body section, and the one end section and the other end section of the absorbent body may be arranged at one end section and the other end section in the longitudinal direction of the main body section, respectively.

In such an absorbent article, it is desirable that a second fluid-absorbent member that absorbs fluid is included inside the main body section.

With such an absorbent article, the main body section serves as a second absorbent body. Therefore, the absorbent article has with a good fluid-absorbing ability.

In such an absorbent article, it is desirable that a face on the opposite side of a face on which the absorbent body is overlapped on the main body section is provided with a fluid-impermeable sheet covering the face on the opposite side.

With such an absorbent article, an undergarment can be effectively prevented from getting dirty with fluid that has been absorbed by the fluid-absorbent member of the absorbent body. This is because, although the undergarment contacts the face on the opposite side of the main body section, in such a state, movement of fluid that has been absorbed by the fluid-absorbent member to the undergarment is blocked by the fluid-impermeable sheet covering the face on the opposite side.

First Embodiment

Absorbent Article 1

An absorbent article 1 is, for example, a sanitary napkin. In the following description, the side that is brought into contact with the human body is referred to as a surface side, the side that is brought into contact with an undergarment 90 is referred to as a back face side, the end section that is positioned on the front side of the human body when worn is referred to as a front end section (corresponding to one end section), and the end section that is positioned on the rear side is referred to as a rear end section (corresponding to the other end section). Furthermore, the normal direction of the surface or the back face of the absorbent article 1 is also referred to as a thickness direction.

Figure 2:
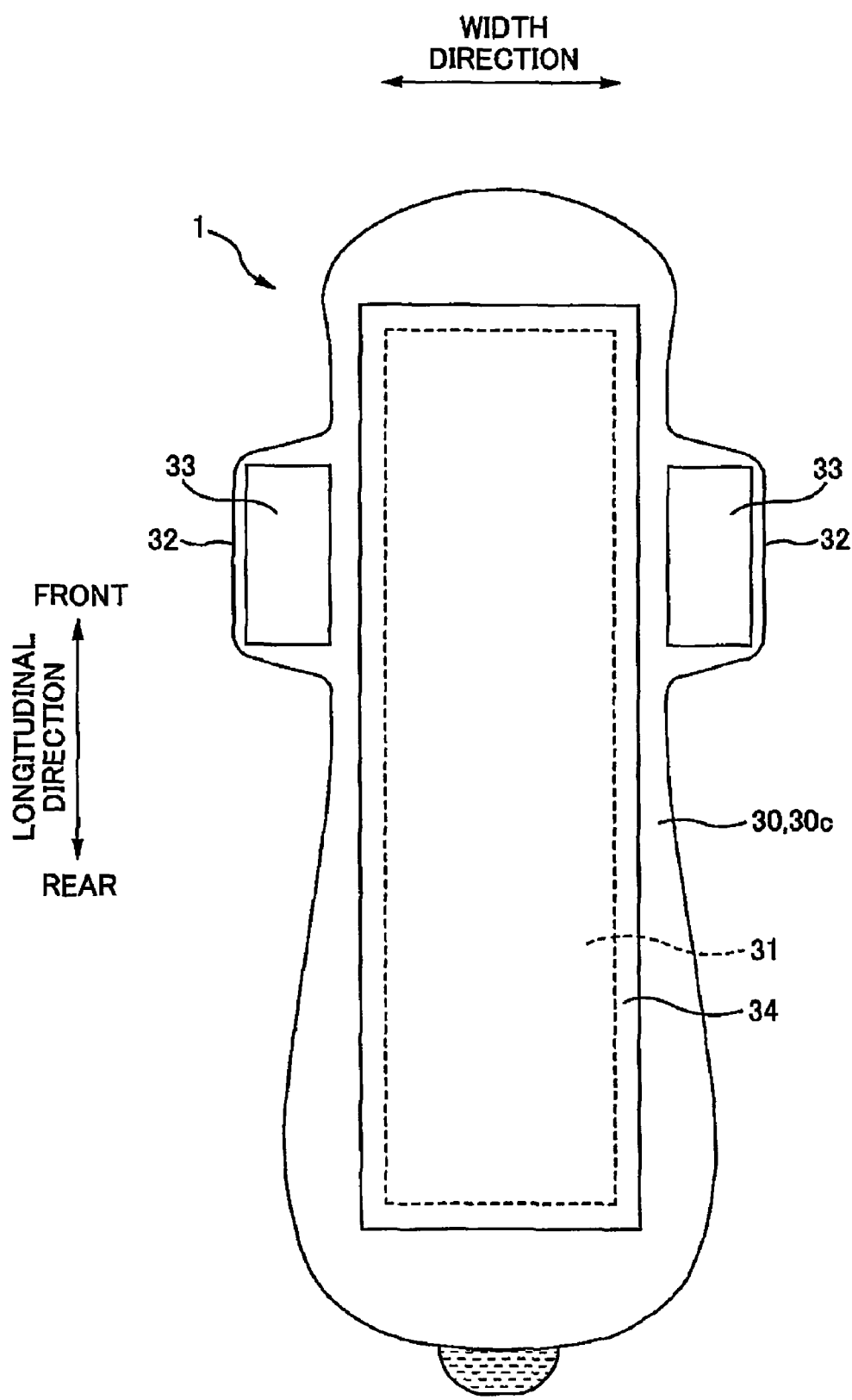
FIG. 2 is a plan view of the back face side of the same absorbent article.
Figure 3:
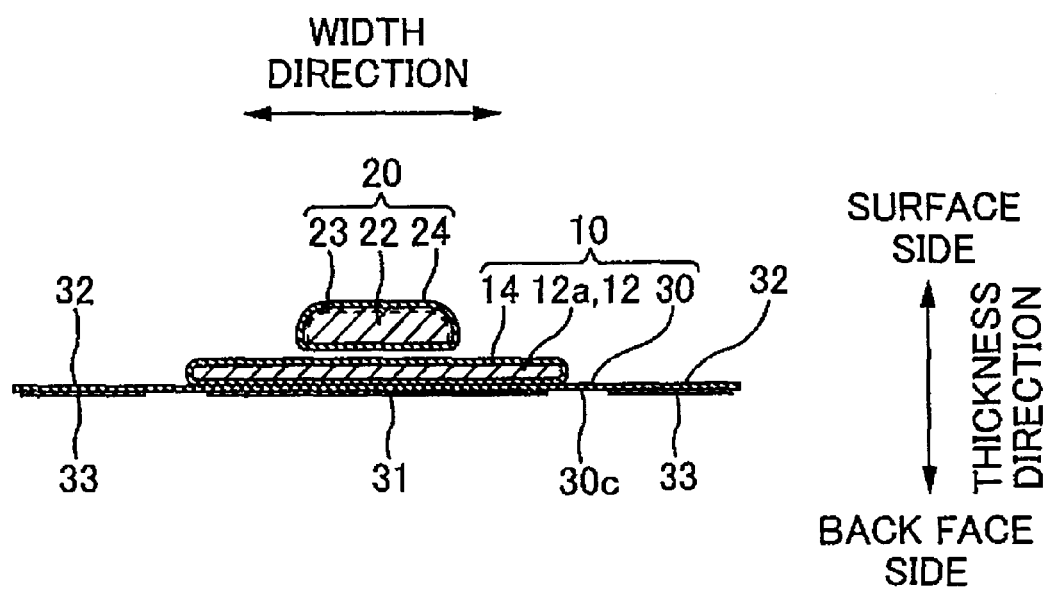
FIG. 3 is a cross-sectional view taken along line III-III in FIG. 1.
Figure 4:
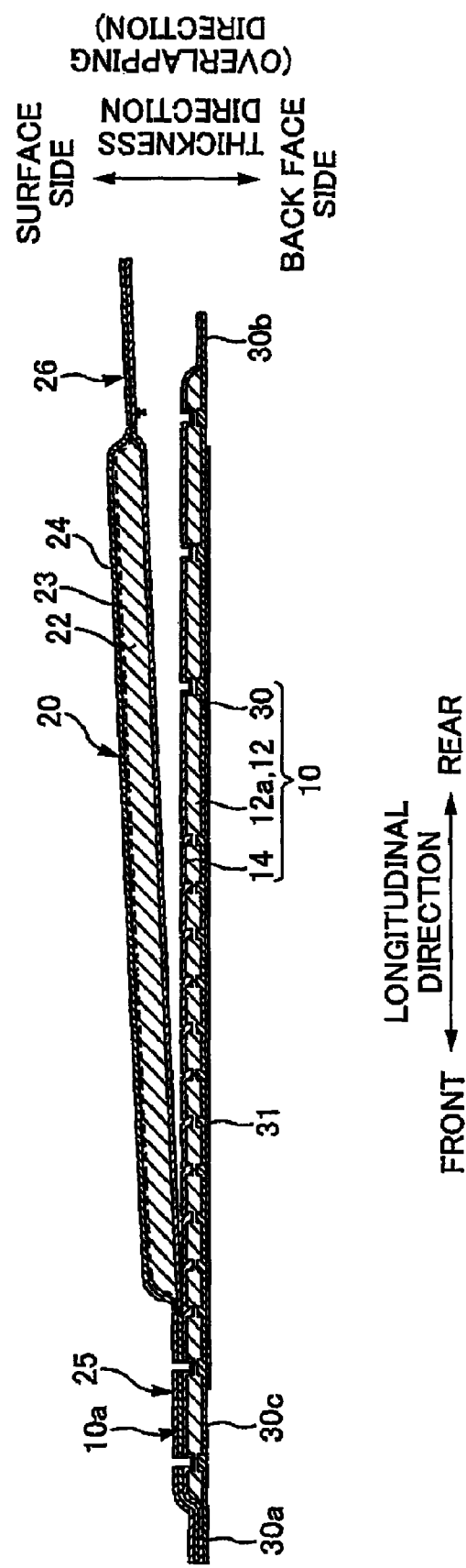
FIG. 4 is a cross-sectional view taken along line IV-IV in FIG. 1.
Figure 5:
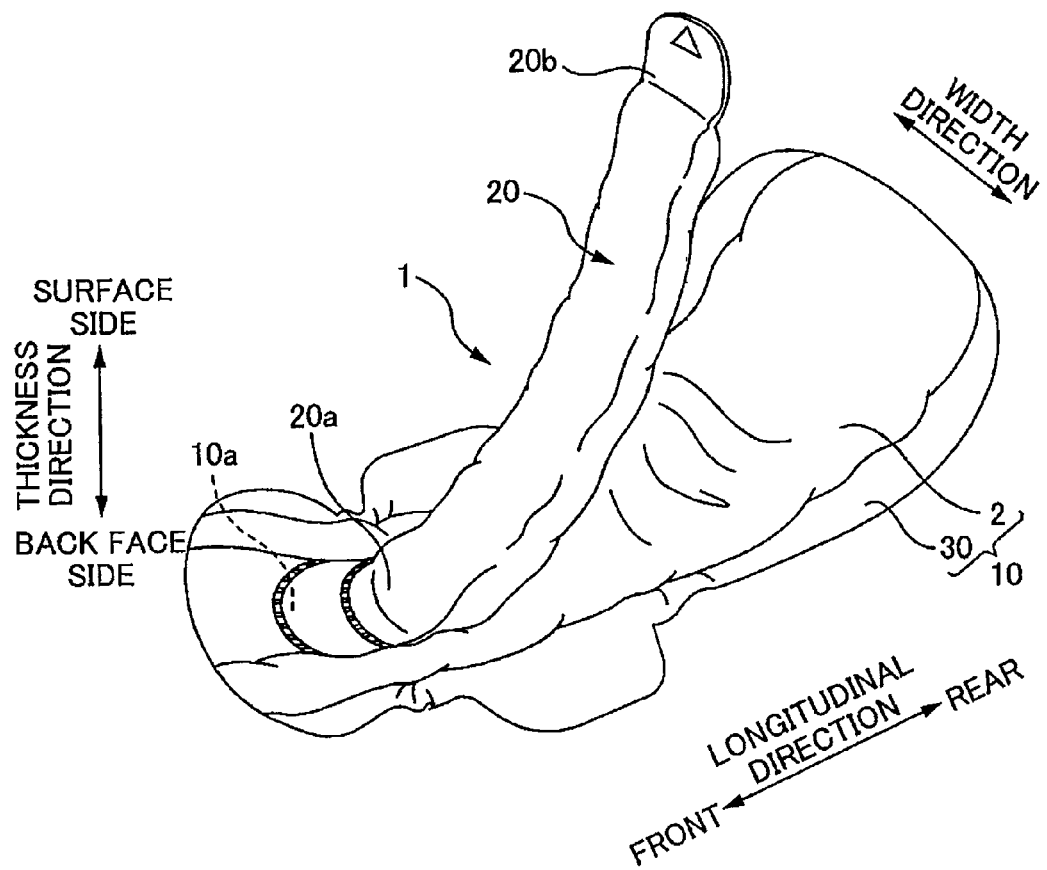
FIG. 5 is a perspective view of the absorbent article 1.

FIG. 1 is a plan view of the surface side of the absorbent article 1 in an unfolded state. FIG. 2 is a plan view of the back face side of this absorbent article. FIG. 3 is a cross-sectional view taken along line III-III in FIG. 1. FIG. 4 is a cross-sectional view taken along line IV-IV in FIG. 1. FIG. 5 is a perspective view of the absorbent article 1. FIGS. 6 to 8A are perspective views of the absorbent article 1, for illustrating a state in use.

As shown in FIGS. 1 and 4, the absorbent article 1 has a shape that is generally elongated in a predetermined direction. As shown in FIG. 5, the absorbent article 1 includes a substantially rectangular-shaped base absorbent body 10 (corresponding to a main body section) for absorbing fluid such as menstrual blood, and a top absorbent body 20 (corresponding to an absorbent body) that is overlapped with the surface of the base absorbent body 10 and disposed in the center in the width direction of the base absorbent body 10 along the longitudinal direction.

Figure 6:
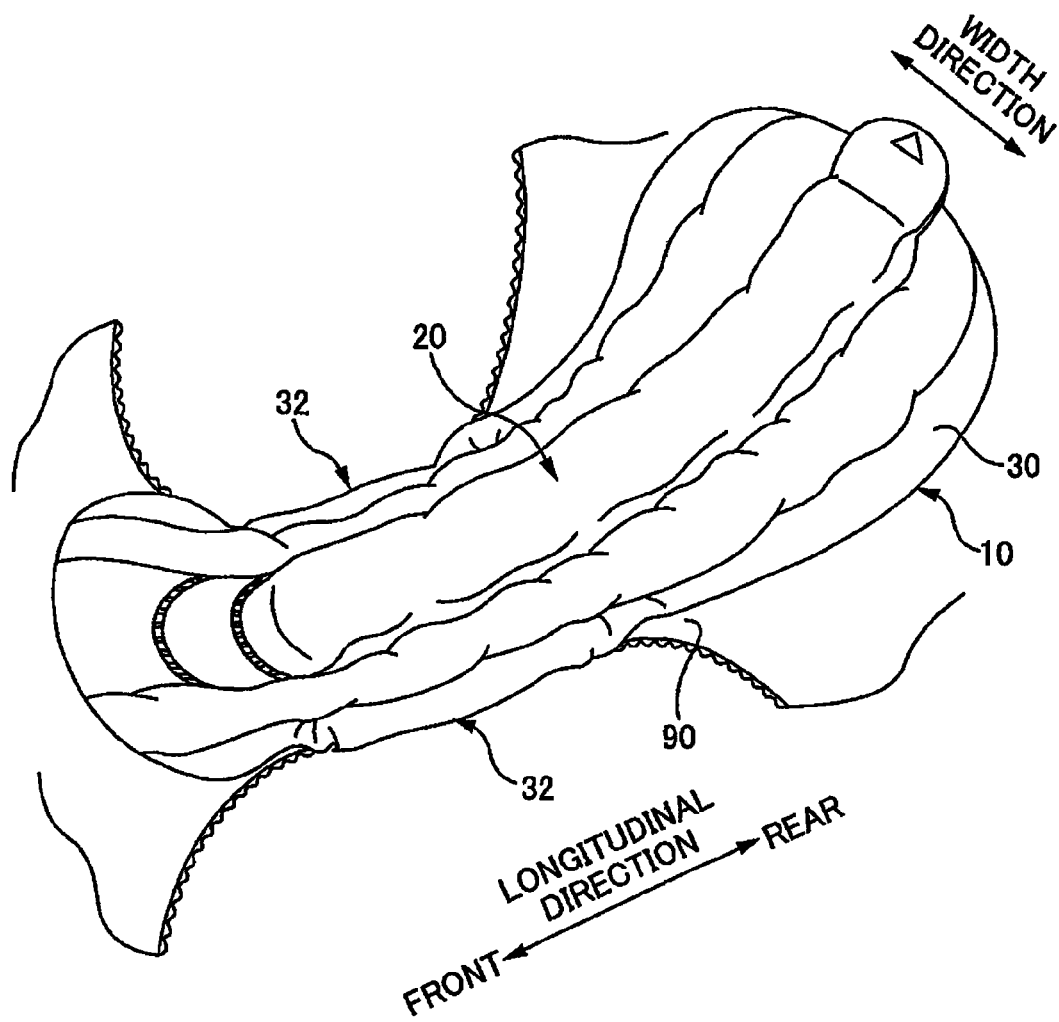
FIG. 6 is a perspective view of the absorbent article 1, for illustrating a state in use.
Figure 7:
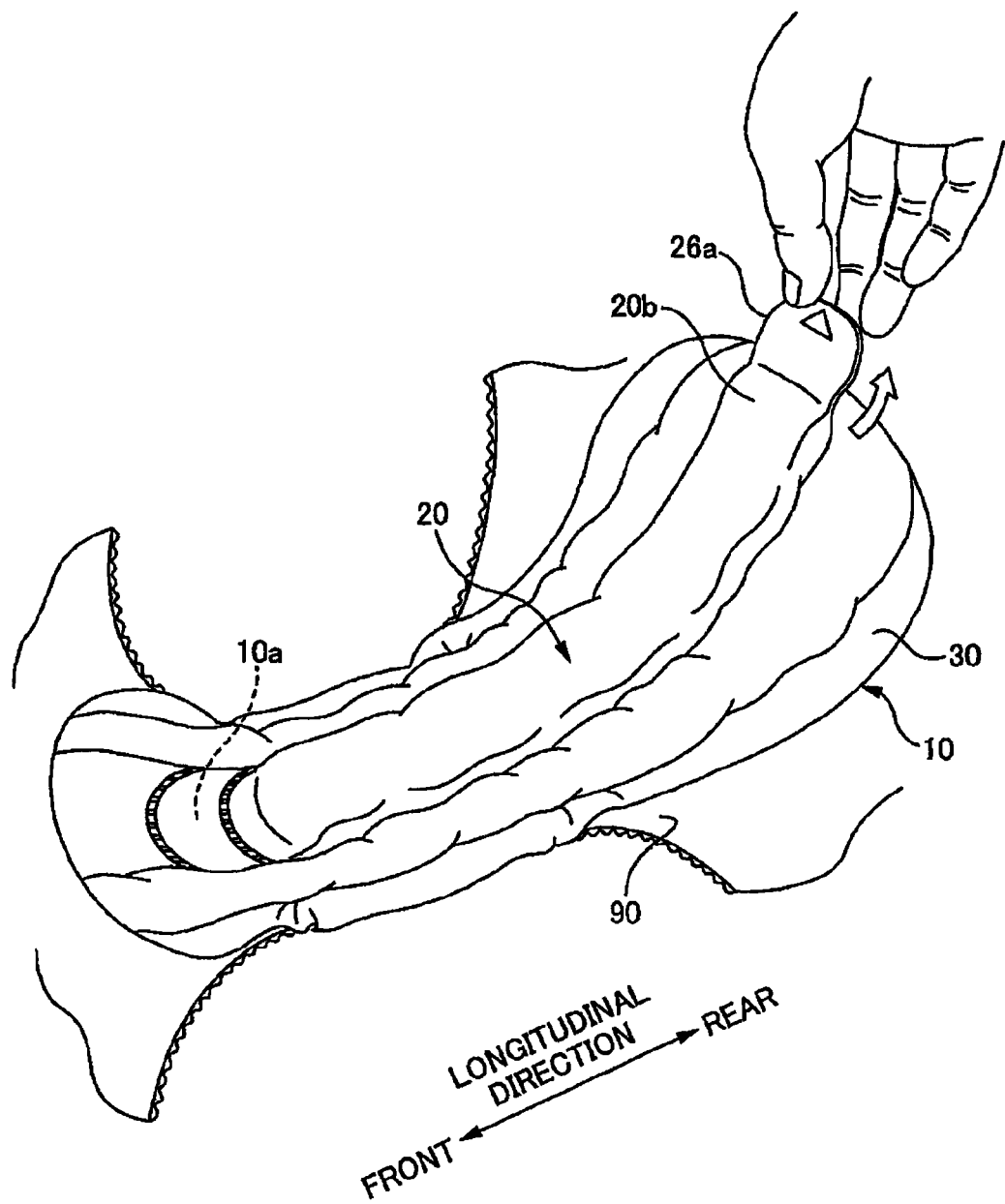
FIG. 7 is a perspective view of the absorbent article 1, for illustrating a state in use.
Figure 8A:
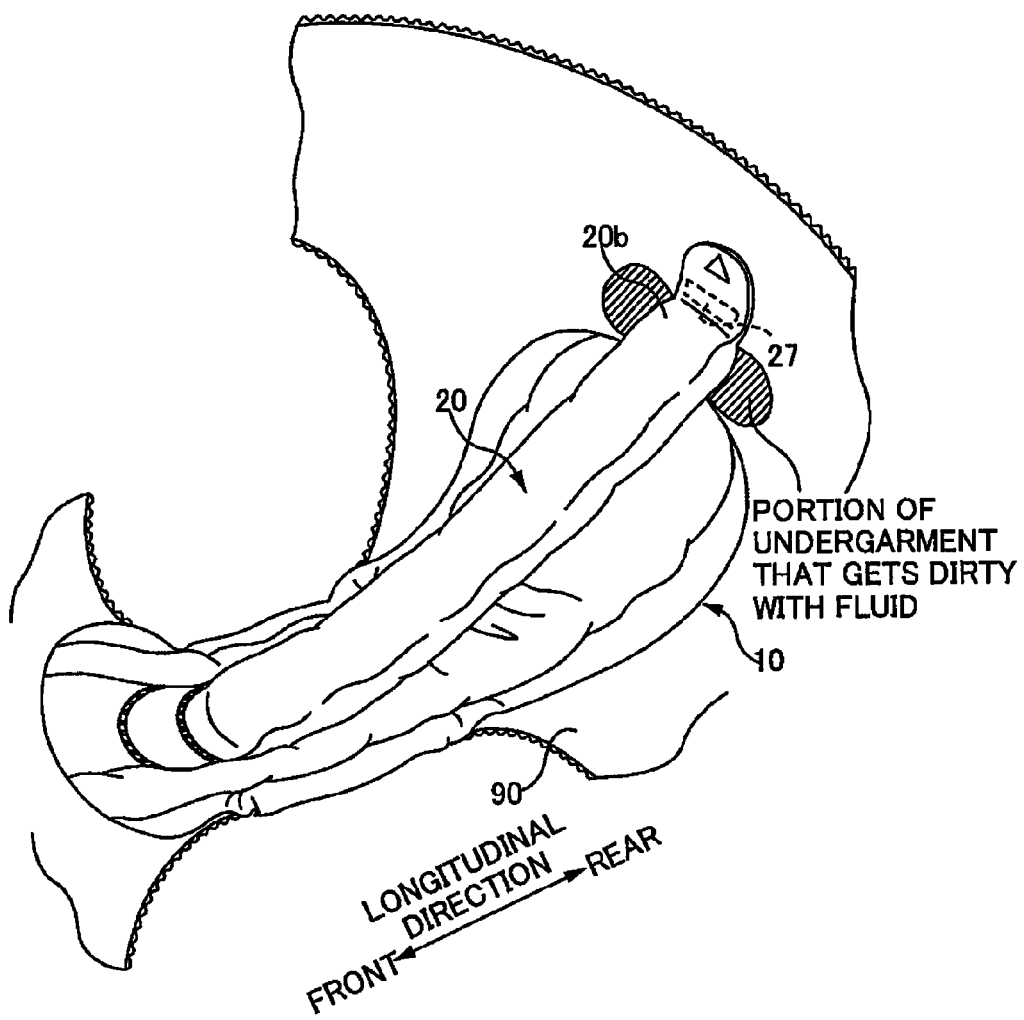
FIG. 8A is a perspective view of the absorbent article 1, for illustrating a state in use.
Figure 8B:
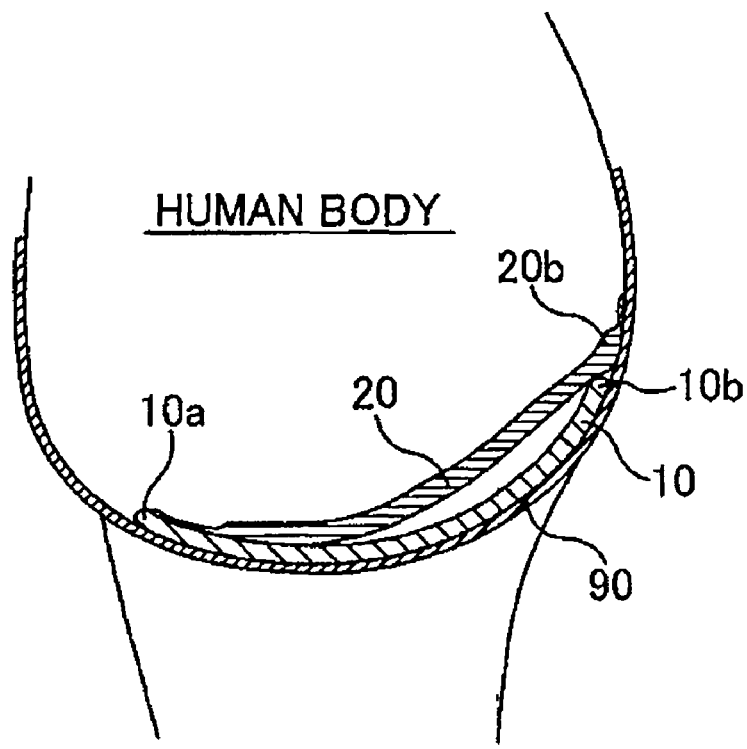
FIG. 8B is a vertical cross-sectional view of the human body, for illustrating a state in use.

Herein, in the top absorbent body 20, a front end section 20a is fixed to a front end section 10a of the base absorbent body 10, and a rear end section 20b is a free end that can be separated from the base absorbent body 10. More specifically, the rear end section 20b of the top absorbent body 20 is movable in the thickness direction that is a direction in which the top absorbent body 20 is overlapped with the base absorbent body 10, or back and forth in the longitudinal direction. Thus, at the time of using the absorbent article 1, as shown in FIG. 6, the base absorbent body 10 is fixed to the inner face of the undergarment 90 while the longitudinal direction of the top absorbent body 20 is disposed along the front-and-rear direction of the human body. Then, in a state where the undergarment 90 is worn, as shown in FIG. 7, the rear end section 20b of the top absorbent body 20 is pulled up, and thus the top absorbent body 20 is placed in the groove of the buttocks and the like. In this state, as shown in FIG. 8A, the rear end section 20b of the top absorbent body 20 is fixedly engaged with the undergarment 90, and thereby the top absorbent body 20 is worn on the human body. Fluid that has been discharged from the groove is absorbed mainly by the top absorbent body 20.

Note that in this worn state, as shown in FIG. 1, a position Z assumed to abut against the human bodily discharge opening, at which the human bodily discharge opening (portion from which the fluid is discharged) is assumed to abut against the absorbent article 1, is positioned closer to the front side than the center in the longitudinal direction, on the center line in the width direction of the absorbent article 1. More specifically, the absorbent article 1 is formed so that the length from the position Z assumed to abut against the human bodily discharge opening to the rear side is longer than the length from the position Z assumed to abut against the human bodily discharge opening to the front side. Hereinafter, each of the elements of the absorbent article 1 is described in detail.

<Base Absorbent Body 10>

As shown in FIGS. 3 and 4, the base absorbent body 10 includes a substantially rectangular plate-shaped absorbent body base material 12 in which a pulverized pulp 12a (corresponding to a second fluid-absorbent member) containing a superabsorbent polymer is wrapped in a fluid-permeable sheet (not shown) such as a tissue paper, a surface sheet 14 that covers at least the entire face on the surface side in the absorbent body base material 12, and a back face sheet 30 for preventing leakage of fluid that has been absorbed by the absorbent body base material 12 to the back face side.

The surface sheet 14 is, for example, a fluid-permeable sheet that is substantially rectangular as the absorbent body base material 12. The surface sheet 14 is made of a material such as an appropriate nonwoven fabric. For example, a spunlaced nonwoven fabric made of cellulose fiber such as rayon, synthetic resin fiber or the like, and air through nonwoven fabric made of synthetic resin fiber or the like are used.

The back face sheet 30 is, for example, a fluid-impermeable sheet made of a material such as polyethylene or polypropylene. The shape of the back face sheet 30 is substantially as long as the absorbent body base material 12 in the longitudinal direction, and wider than the absorbent body base material 12 in the width direction. As shown in FIG. 4, in a state where the absorbent body base material 12 is placed on the surface of the back face sheet 30, the back face sheet 30 is joined to the surface sheet 14 at least at a front end section 30a and a rear end section 30b, and thus the absorbent body base material 12 is held between the back face sheet 30 and the surface sheet 14.

Note that, as shown in FIGS. 2 to 4, an undergarment fixation adhesive 31 for fixing the absorbent article 1 to the inner face of the undergarment 90 at the time of use is applied to a back face 30c of the back face sheet 30. The region where the undergarment fixation adhesive 31 is applied corresponds to the position where the absorbent body base material 12 is disposed on the surface side. Furthermore, in order to more firmly fix the absorbent article 1 to the undergarment 90, wing sections 32 extended outward in the width direction are formed on both ends in the width direction of the back face sheet 30. Undergarment fixation adhesives 33 are applied to the back face of the wing sections 32. In the case of fixing the absorbent article 1 to the undergarment 90, these wing sections 32, 32 are folded outward, and are fixed to the outer face of the undergarment 90 with the undergarment fixation adhesives 33. It should be noted that, before use, protection sheets 34 and 35 for protecting viscosity are attached to the regions to which the undergarment fixation adhesives 31 and 33 have been applied (refer to FIGS. 2 and 11). These protection sheets 34 and 35 are removed immediately before using the absorbent article 1.

<Top Absorbent Body 20>

Figure 9:
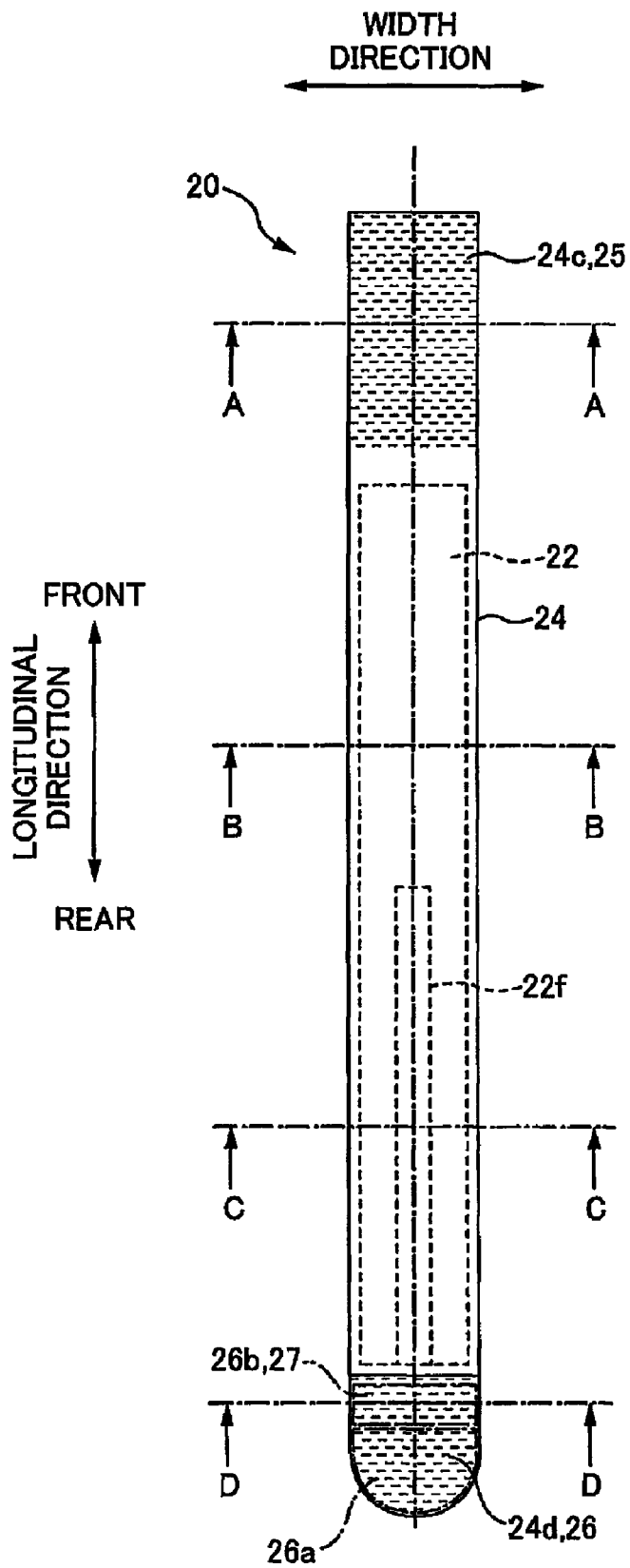
FIG. 9 is a plan view of a top absorbent body 20 in an unfolded state.

FIG. 9 is a plan view of the top absorbent body 20 in an unfolded state. Further, FIGS. 10A to 10D are cross-sectional views respectively taken along lines A-A, B-B, C-C, and D-D in FIG. 9.

Figure 10A:
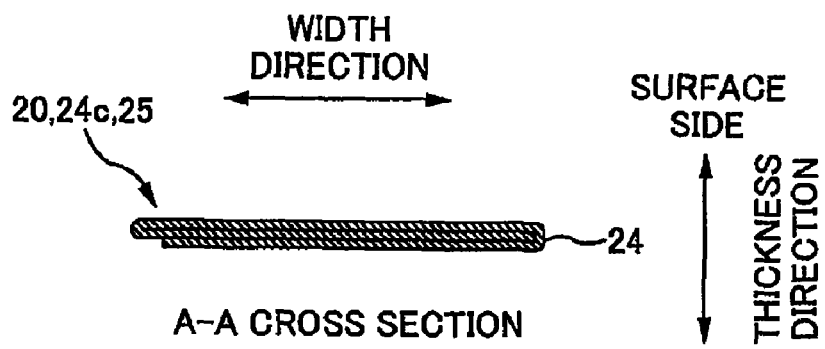
FIG. 10A is a cross-sectional view taken along line A-A in FIG. 9.
Figure 10B:
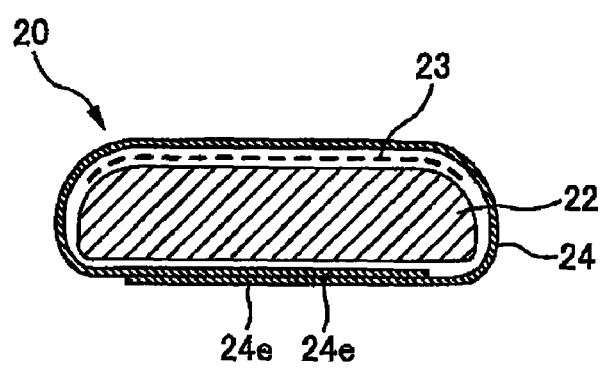
FIG. 10B is a cross-sectional view taken along line B-B in FIG. 9.
Figure 10C:
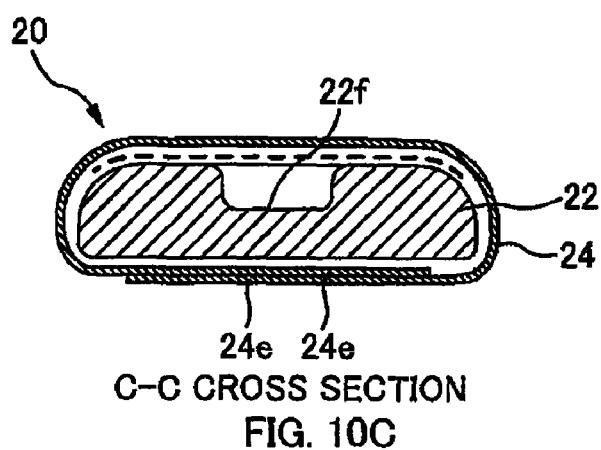
FIG. 10C is a cross-sectional view taken along line C-C in FIG. 9.

As shown in FIGS. 9, 10B, and 10C, the top absorbent body 20 includes a pulverized pulp 22 (corresponding to a fluid-absorbent member that absorbs fluid) containing a superabsorbent polymer, an intermediate sheet 23 that is disposed closer to the surface side than the pulverized pulp 22, and a shape retaining sheet 24 for collectively wrapping around the pulverized pulp 22 and the intermediate sheet 23 thereby retaining these pulverized pulp 22 and the like in a long article body that is long in the longitudinal direction.

The intermediate sheet 23 is a rectangular fluid-permeable sheet that can retain more fluid than the shape retaining sheet 24. For example, the material of the intermediate sheet 23 is the same as that of the shape retaining sheet 24, but the intermediate sheet 23 is a denser sheet than the shape retaining sheet 24.

The shape retaining sheet 24 is a fluid-permeable sheet. The shape retaining sheet 24 is made of a material such as an appropriate nonwoven fabric. For example, the spunlaced nonwoven fabric made of cellulose fiber such as rayon, synthetic resin fiber or the like, and the air through nonwoven fabric made of synthetic resin fiber or the like are used. The shape viewed from above of the shape retaining sheet 24 that has been unfolded into a flat sheet is substantially rectangular (refer to FIG. 14). In a state where end sections 24e on both ends in the width direction of the shape retaining sheet 24 are overlapped and joined to each other by a hot-melt adhesive, so that the shape retaining sheet 24 is formed into a tubular shape as shown in FIGS. 10B and 10C the pulverized pulp 22 and the intermediate sheet 23 are contained inside the shape retaining sheet 24 along the longitudinal direction. Note that, in a state where the top absorbent body 20 is disposed on the base absorbent body 10, as shown in FIGS. 10B and 10C, the section in which the end sections 24e on both sides in the width direction of the shape retaining sheet 24 are overlapped and joined to each other is positioned closer to the back face than the pulverized pulp 22.

Figure 10D:
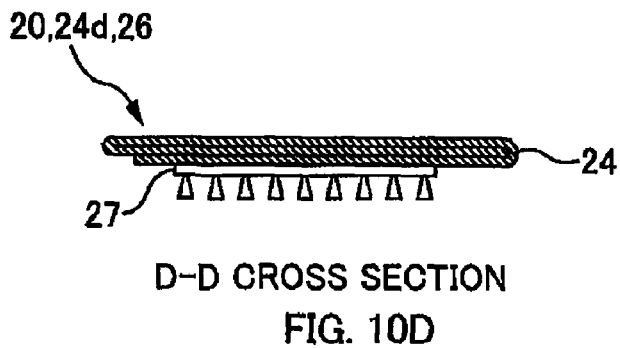
FIG. 10D is a cross-sectional view taken along line D-D in FIG. 9.

Furthermore, a front end section 24c and a rear end section 24d in the longitudinal direction of the shape retaining sheet 24 shown in FIG. 9 are each folded in a state not containing the pulverized pulp 22 or the intermediate sheet 23, as shown in FIGS. 10A and 10D, and embossing is performed in a state where an adhesive (not shown) is interposed between the folded sections 24c and 24d. Accordingly, in the front end section and the rear end section in the longitudinal direction of the shape retaining sheet 24, thin sealed sections 25 and 26 for sealing these end sections are formed (refer to FIG. 9).

As shown in FIG. 1, the top absorbent body 20 has substantially the same length as the base absorbent body 10 in the longitudinal direction, but it is narrower than the base absorbent body 10 in the width direction. The top absorbent body 20 is disposed in the middle in the width direction of the base absorbent body 10. As shown in FIGS. 1 and 4, the front sealed section 25 of the top absorbent body 20 is firmly fixed to the front end section 10a of the base absorbent body 10, but the rear sealed section 26 is formed so that it can be moved apart from the base absorbent body 10.

Note that, before use, the rear sealed section 26 is temporarily fixed to the base absorbent body 10 so as to be separable therefrom with a small force. In this temporarily fixed state, the rear sealed section 26 is projected rearward only by approximately 20 mm from the external outline of the base absorbent body 10 so that it can be picked up by the user. More specifically, the rear end portion of the rear sealed section 26 functions as a pick-up section 26a that is to be picked up by the user, at the time of wearing the absorbent article and the like. Furthermore, as shown in FIGS. 9 and 10D, in a section 26b on the front side in the rear sealed section 26, which is a portion opposing the base absorbent body 10, a hook member 27 for engaging the rear end of the top absorbent body 20 with the undergarment 90 in use is provided. The hook member 27 is, for example, a male member of a mechanical fastener.

By the way, the hook member 27 may be provided in a portion other than the sealed section 26. For example, the hook member 27 may be provided in a portion on the back face side of the top absorbent body 20, whose surface side has the pulverized pulp 22. At that time, a portion of the base absorbent body 10 opposing the hook member 27 may be provided with an engagement member that is to be engaged with the hook member 27. If the hook member 27 is the male member of the mechanical fastener, a female member of the mechanical fastener is used as the engagement member, for example.

Moreover, the top absorbent body 20 that is worn is sandwiched in the groove of the buttocks and the like. Thus, the top absorbent body 20 can be fixed to the human body even without the hook member 27. In other words, the hook member 27 is not an essential configuration, and may be omitted.

Furthermore, as shown in FIGS. 9 and 10C, it is desirable that in a region on the rear side of the top absorbent body 20, in the middle section in the width direction a thin wall section 22f is formed in which the amount of the pulverized pulp 22 is smaller than in other portions in the width direction. With the thin wall section 22f, the top absorbent body 20 is easily bent to form a peak, and is easily placed in the groove of the buttocks and the like of the human body. Herein, as described above, if the hook member 27 is provided in a portion on the back face side of the top absorbent body 20, whose surface side has the pulverized pulp 22, it is preferable that the thin wall section 22f is not formed in the portion provided with the hook member 27. The reason for this is that if the top absorbent body 20 is easily bent to form a peak up to the hook member 27, it is difficult for the hook member 27 to be engaged with the base absorbent body 10. For example, it is preferable that in the top absorbent body 20, the thin wall section 22f is not formed in the portion provided with the hook member 27 and at the rear of this portion.

<<Wrapping of the Absorbent Article 1>>

Figure 11:
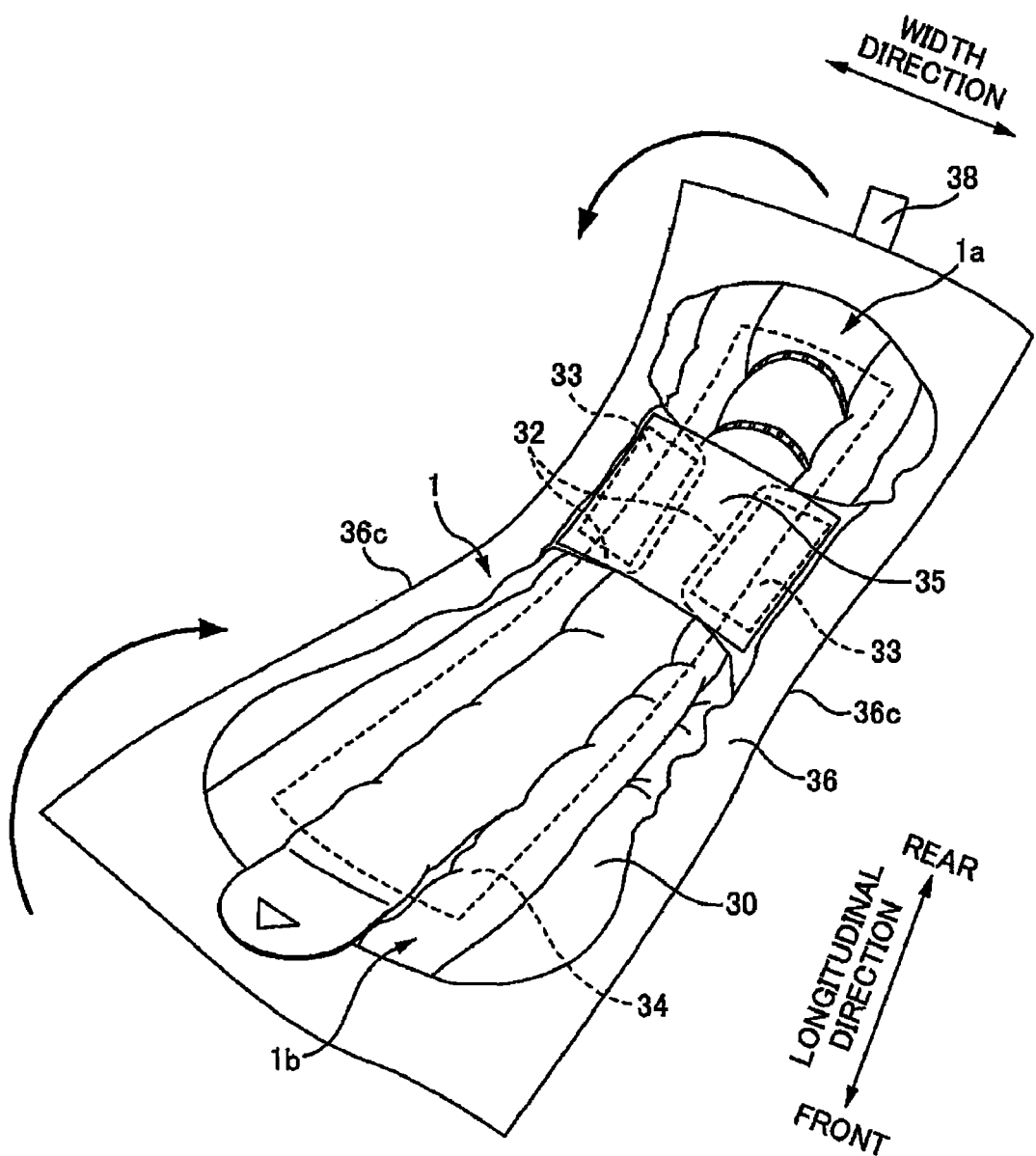
FIG. 11 is a view showing the manner in which the absorbent article 1 is wrapped.

FIG. 11 is a view showing the manner in which the absorbent article 1 is wrapped. As shown in FIG. 11, in the case where the absorbent article 1 is wrapped, each of the wing sections 32 on both sides of the absorbent article 1 are bent toward the surface side, and a protection sheet 35 is placed from the surface side covering the undergarment fixation adhesives 33 of the wing sections 32 which are bent. Also, a protection sheet 34 is placed to cover the region to which the undergarment fixation adhesive 31 has been applied, on the back face 30c of the back face sheet 30. And, in this state, the absorbent article 1 is folded in three, together with a substantially rectangular-shaped wrapping sheet 36 disposed on the back face side, so that a front end section 1a and a rear end section 1b are on the surface side. In a state where the absorbent article 1 has been folded in three, a lead tape 38 provided at the front end of the wrapping sheet 36 is attached to the outer face of the wrapping sheet 36 on the side of the rear end that has been already bent, and then edge sections 36c along the longitudinal direction are caused to adhere and seal, and thus the wrapping sheet 36 is formed into a package-shape. Thereby, the absorbent article 1 is in a wrapped state.

<<Wearing of the Absorbent Article 1 on a Human Body>>

The absorbent article 1 that has been supplied to the user in the above wrapped state is taken out from the wrapping sheet 36, by the user removing the lead tape 38 so that the wrapping sheet 36 is unfolded as shown in FIG. 11.

First, the protection sheet 34 of the absorbent article 1 is removed, and the undergarment fixation adhesive 31 on the back face 30c of the back face sheet 30 is exposed (FIG. 2). After that, as shown in FIG. 6, the absorbent article 1 is disposed on the inner face of the undergarment 90 and is fixed by the undergarment fixation adhesive 31. And at that time, the protection sheet 35 of the wing sections 32 is also removed, and the undergarment fixation adhesives 33 are exposed. And the wing sections 32 are folded toward the undergarment 90 side and are fixed by the undergarment fixation adhesives 33 to the outer face of the undergarment 90.

In the case where the absorbent article 1 is fixed to the undergarment 90 in this manner, the undergarment 90 is pulled up toward the human body side, that is, the undergarment 90 is worn by the user. In this state, as shown in FIG. 7, the pick-up section 26a of the top absorbent body 20 is picked up and the top absorbent body 20 is pulled up by the user. Thereby, the temporary fixation between the base absorbent body 10 and the top absorbent body 20 is cancelled, and the rear end section 20b of the top absorbent body 20 is separated from the base absorbent body 10.

Subsequently, by the user moving the pick-up section 26a in the longitudinal direction (substantially the vertical direction), the position of the top absorbent body 20 is adjusted so that the top absorbent body 20 is in close contact with the groove of the buttocks and the like of the human body. After the position of the top absorbent body 20 has been adjusted, the hook member 27 of the top absorbent body 20 is fixed to the human body-side face of the back body of the undergarment 90 or the edge section of the undergarment 90, as shown in FIG. 8A. Accordingly, the top absorbent body 20 is positioned to preferably abutting against the human body.

<<Problem in the State where the Absorbent Article 1 is Worn on a Human Body>>

In a state where the absorbent article 1 is unfolded and has not been worn yet, as shown in FIG. 1, the rear end section 20b of the top absorbent body 20 is positioned in the vicinity of the external outline of the base absorbent body 10, that is, the rear end section 20b is not substantially projected rearward from the external outline. However, in the worn state of the absorbent article 1 shown in FIG. 8A, the rear end section 20b of the top absorbent body 20 is projected rearward by a predetermined length from the external outline of the base absorbent body 10. This is because, as shown in the vertical cross-sectional view of the human body in FIG. 8B, the base absorbent body 10 is disposed with a small radius of curvature along the inner face of the undergarment 90, while the top absorbent body 20 is placed in the groove of the buttocks and the like to connect the front end section 10a and a rear end section 10b of the base absorbent body 10 with a short path which is a substantially straight line with a large radius of curvature, that is, a path in the inner side of the human body that is shorter than the path along the inner face of the undergarment 90.

In the case where the rear end section 20b of the top absorbent body 20 is projected from the external outline of the base absorbent body 10 in this way, the outer face on the side of the base absorbent body 10 (that is, the outer face on the back face side) of the rear end section 20b is brought into direct contact with the undergarment 90. In this situation, if fluid that has been absorbed by the pulverized pulp 22 of the top absorbent body 20 oozes out to the outer face of the rear end section 20b of the top absorbent body 20, the undergarment 90 may get dirty with the fluid.

Thus, as in the following description, in the absorbent article 1 according to the first embodiment, the rear end section 20b of the top absorbent body 20 is provided with a fluid-impermeable layer 50, and thus fluid is prevented from oozing out to the outer face of the rear end section 20b. As a result, the undergarment 90 is prevented from getting dirty with fluid that has been absorbed by the top absorbent body 20.

Herein, also in this worn state, if the top absorbent body 20 is not substantially projected from the external outline of the base absorbent body 10 as shown in FIG. 1, the undergarment 90 is unlikely to get dirty. This is because, as shown in FIG. 3, the back face side of the base absorbent body 10 is covered with the fluid-impermeable back face sheet 30, and the back face sheet 30 blocks movement of fluid that has been absorbed by the top absorbent body 20 or the base absorbent body 10 toward the undergarment 90 side.

<<Fluid-Impermeable Layer 50 of the Top Absorbent Body 20 According to the First Embodiment>>

Figure 12:
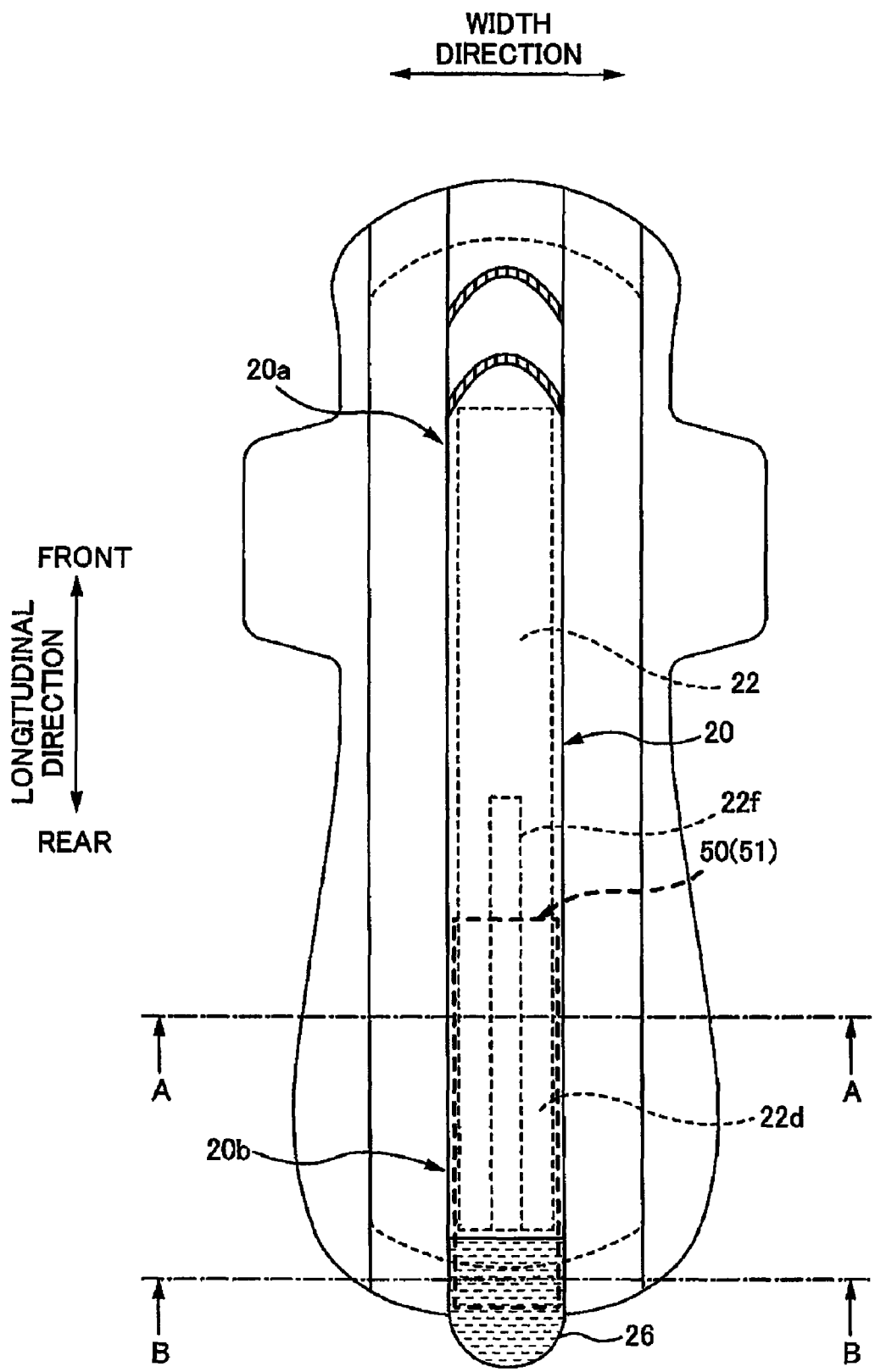
FIG. 12 is an explanatory view of a fluid-impermeable layer 50 of the top absorbent body 20 according to the first embodiment, and is a plan view of the surface side of the unfolded absorbent article 1.
Figure 13A:
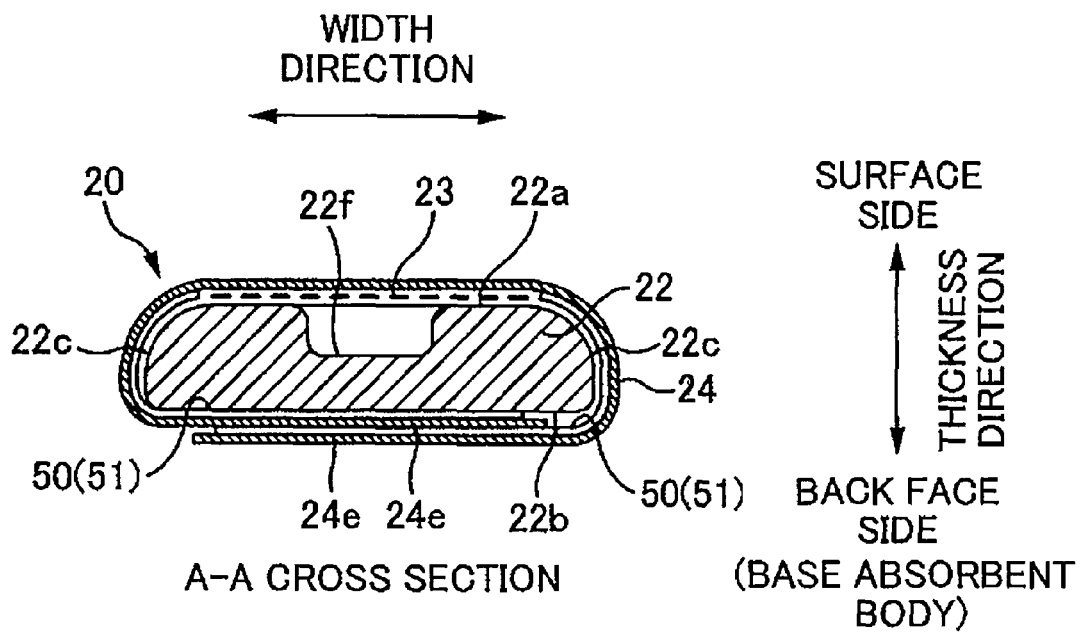
FIG. 13A is a cross-sectional view showing only the top absorbent body 20, taken along line A-A in FIG. 12.
Figure 13B:
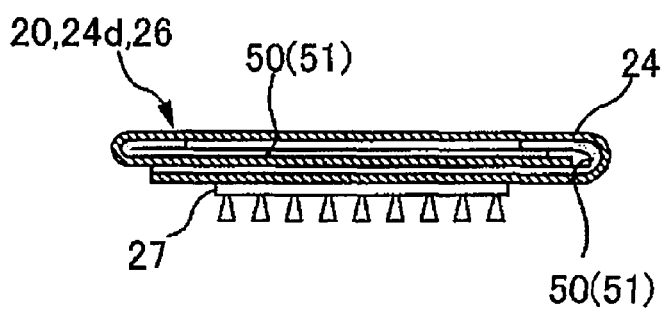
FIG. 13B is a cross-sectional view showing only the top absorbent body 20, taken along line B-B in FIG. 12.

FIGS. 12 to 13B are explanatory views of the fluid-impermeable layer 50 of the top absorbent body 20 according to the first embodiment. FIG. 12 is a plan view of the surface side of the absorbent article 1 in an unfolded state. FIG. 13A is a cross-sectional view showing only the top absorbent body 20, taken along line A-A in FIG. 12. FIG. 13B is a cross-sectional view showing only the top absorbent body 20, taken along line B-B in FIG. 12.

The fluid-impermeable layer 50 according to the first embodiment is included at the rear end section 20b of the top absorbent body 20 in the longitudinal direction as shown in FIG. 12, and is included covering a portion closer to the base absorbent body 10 than the pulverized pulp 22 of the top absorbent body 20 (that is, a portion on the back face side) in the thickness direction that is a direction in which the top absorbent body 20 is overlapped with the base absorbent body 10, as shown in FIG. 13A.

Thus, the fluid-impermeable layer 50 can suppress fluid oozing to the outer face on the side of the base absorbent body 10, in the rear end section 20b of the top absorbent body 20. As a result, in a state where the absorbent article 1 is worn on the human body, even if the rear end section 20b of the top absorbent body 20 is projected rearward from the external outline of the base absorbent body 10 as shown in FIG. 8A, fluid does not ooze out at least to the outer face on the side of the base absorbent body 10, which may be brought into contact with the undergarment 90, in the rear end section 20b. Thus, the undergarment 90 is effectively prevented from getting dirty.

Furthermore, as shown in FIG. 13A, the fluid-impermeable layer 50 is provided covering at least a portion closer to the base absorbent body 10 than the pulverized pulp 22 of the top absorbent body 20. Therefore, there is no need to provide an area with no pulverized pulp 22 disposed regarding the longitudinal direction (refer to FIG. 12). Accordingly, the pulverized pulp 22 in an amount corresponding to the total length of the top absorbent body 20 can be maintained, and thus the amount of fluid that can be absorbed by the top absorbent body 20 does not have to decrease in accordance with formation of the fluid-impermeable layer 50.

Hereinafter, the fluid-impermeable layer 50 is described in detail.

As shown in FIG. 12, the fluid-impermeable layer 50 according to the first embodiment covers only a rear end section 22d in the longitudinal direction in the pulverized pulp 22, and is extended from this position to a part of the rear sealed section 26. Furthermore, as shown in FIG. 13A, regarding the thickness direction, the fluid-impermeable layer 50 is provided throughout the entire periphery of the outer peripheral face of the pulverized pulp 22, excluding an area of a predetermined width from the middle of a surface 22a in the width direction. More specifically, the fluid-impermeable layer 50 is provided covering a back face 22b and side faces 22c on both sides in the width direction, substantially excluding the surface 22a of the pulverized pulp 22.

Herein, as shown in FIG. 13A, the surface 22a of the pulverized pulp 22 (corresponding to a portion that is closer to the human body side than the pulverized pulp 22 in the thickness direction, or a portion that is farther from the base absorbent body 10 than the pulverized pulp 22 in the thickness direction) is provided with an area with no fluid-impermeable layer 50 disposed like such. This is because, through the area with no fluid-impermeable layer 50 disposed, fluid that has been discharged from the human body that is positioned on the side of the surface 22a can be directly absorbed by the pulverized pulp 22.

Furthermore, here, the fluid-impermeable layer 50 covers not only the back face 22b of the pulverized pulp 22 but also the side faces 22c on both sides in the pulverized pulp 22. Thus, the undergarment 90 is more unlikely to get dirty.

The above fluid-impermeable layer 50 may be provided covering the outer peripheral face of the shape retaining sheet 24, however, it is preferably formed interposed between the inner peripheral face of the shape retaining sheet 24 and the outer peripheral face of the pulverized pulp 22 as shown in FIG. 13A. The reason for this is because, if the fluid-impermeable layer 50 is formed inside the shape retaining sheet 24, the shape retaining sheet 24 contacts with the human body, and the fluid-impermeable layer 50 does not contact with the human body at all. And as a result, in the case of choosing the material of the fluid-impermeable layer 50, since there is no need to consider its texture, the degree of freedom in choosing the material of the fluid-impermeable layer 50 increases.

Herein, as a method for forming the fluid-impermeable layer 50, for example, methods are conceivable in which the shape retaining sheet 24 itself is treated to repel water, or in which the shape retaining sheet 24 is covered with a leakage prevention sheet 51. However, here, the latter method is adopted. This is because, according to the latter method, it is possible to further increase leakage resistance, and to easily form the fluid-impermeable layer 50 by merely attaching the leakage prevention sheet 51 to the shape retaining sheet 24, which enables the absorbent article 1 to be mass produced in an excellent manner, as described later in a "method for producing the absorbent article 1".

The leakage prevention sheet 51 is a fluid-impermeable sheet, wherein its material includes, for example, a non-porous film such as polyethylene, polypropylene and the like. Note that, the leakage prevention sheet 51 may have openings that do not let fluid pass through. In this case, it has excellent air permeability.

Furthermore, if the color of the shape retaining sheet 24 is white, in order to make the red color of fluid that has been absorbed by the pulverized pulp 22 less noticeable, the color of the leakage prevention sheet 51 is preferably a color other than white or red, more preferably blue, dark blue, indigo blue, or the like. With these colors, the red color is less noticeable on the back face or the side face of the top absorbent body 20, and relief regarding appearance can be given to the user.

Figure 14:
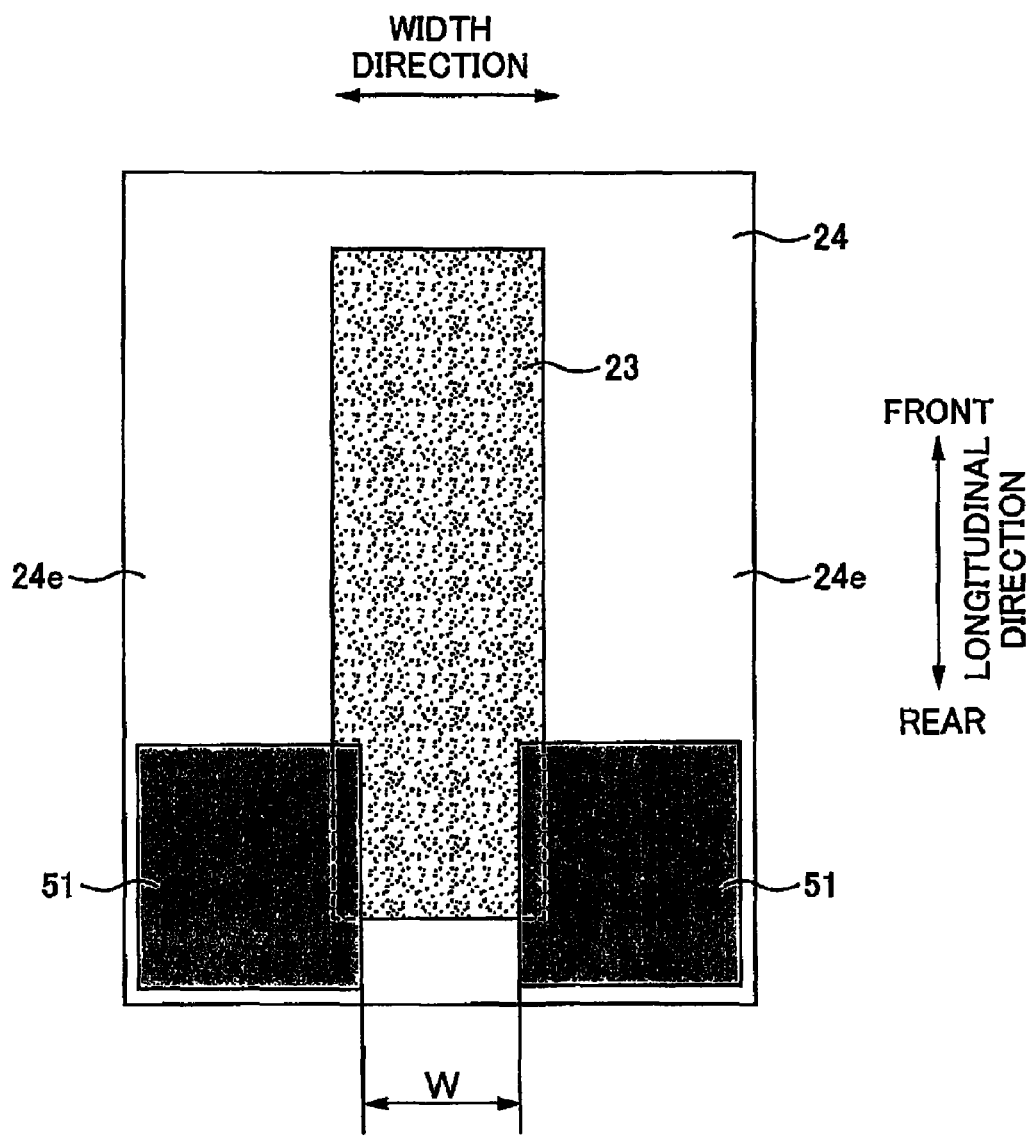
FIG. 14 is an explanatory view of a method for arranging a leakage prevention sheet 51 between a shape retaining sheet 24 and a pulverized pulp 22.

The following is a method for disposing the leakage prevention sheet 51 between the shape retaining sheet 24 and the pulverized pulp 22 as shown in FIG. 13A. First, as shown in FIG. 14, each rectangular leakage prevention sheets 51 is attached to each end sections 24e on both sides in the width direction of the rectangular shape retaining sheet 24 that has been unfolded flat, so that a spacing W is interposed between both of the leakage prevention sheets 51. At that time, regarding the position in the longitudinal direction, both leakage prevention sheets 51 are positioned at the rear end section of the shape retaining sheet 24. Then, a hot-melt adhesive is applied to at least one of the end sections 24e on both sides in the width direction, and the shape retaining sheet 24 is curved into a tubular-form while the face to which the leakage prevention sheets 51 are attached is oriented to the inside. Subsequently, the end sections 24e on both sides in the width direction are overlapped and joined to each other by the hot-melt adhesive. Accordingly, as shown in FIG. 13A, the leakage prevention sheets 51 are positioned on the inner peripheral face of the shape retaining sheet 24.

By the way, in here, the spacing W is provided between the leakage prevention sheets 51 in the width direction. Thus, the area with no leakage prevention sheet 51 disposed in FIG. 13A is also secured on the surface side of the shape retaining sheet 24. Furthermore, the end sections 24e on both sides of the shape retaining sheet 24 are overlapped one on another on the back face side of the top absorbent body 20. Therefore, in this overlapped portion, two leakage prevention sheets 51 are overlapped on each other substantially, and thus leakage can be prevented more effectively. Moreover, the leakage prevention sheets 51 extend to the vicinity of the rear end of the shape retaining sheet 24 as shown in FIG. 14. Thus, as shown in FIG. 13B, the leakage prevention sheets 51 are disposed also to the rear sealed section 26 of the top absorbent body 20. Accordingly, leakage resistance can be secured substantially to the rearmost end of the top absorbent body 20.

Herein, the fluid-impermeable layer 50 (the leakage prevention sheet 51) according to the first embodiment was provided only at the rear end section 20b of the top absorbent body 20 in the longitudinal direction as shown in FIG. 12. However, it is also possible to provide the fluid-impermeable layer 50, not only in the rear end section 20b, but also in the rear half section of the top absorbent body 20, by extending and forming the fluid-impermeable layer 50 forward from the rear end section 20b. Moreover, it is also possible to provide the fluid-impermeable layer 50 throughout the entire length in the longitudinal direction of the top absorbent body 20, by extending it up to the front end section 20a of the top absorbent body 20. However, if the fluid-impermeable layer 50 is extended forward in this way, an area in which movement of fluid is hampered between the top absorbent body 20 and the base absorbent body 10 extends accordingly. Thus, it is desirable that, as in the above-mentioned first embodiment, the fluid-impermeable layer 50 is provided only in the rear end section 20b of the top absorbent body 20.

<<Method for Producing the Absorbent Article 1>>

Figure 15:
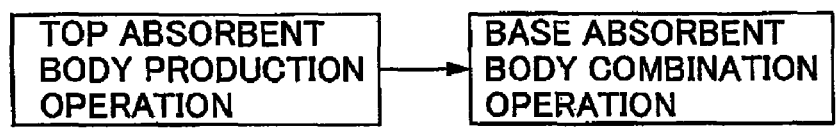
FIG. 15 is a flowchart of a method for producing the absorbent article 1 that includes the fluid-impermeable layer 50 according to the first embodiment.

FIG. 15 is a flowchart of a method for producing the absorbent article 1 that includes the fluid-impermeable layer 50 according to the first embodiment. The method for producing the absorbent article 1 includes a "top absorbent body production process" of producing a continuous body 21 of the top absorbent bodies 20 (in which the top absorbent bodies 20 are continuously arranged in the front-and-rear direction), and a "base absorbent body combination operation" of combining the base absorbent body 10 that has been produced in a base absorbent body production line with the top absorbent body 20 to form the absorbent article 1.

Hereinafter, each process will be described, however, a description of the base absorbent body production line is omitted since it is the same as that of a conventional absorbent article 1.

Figure 16A:
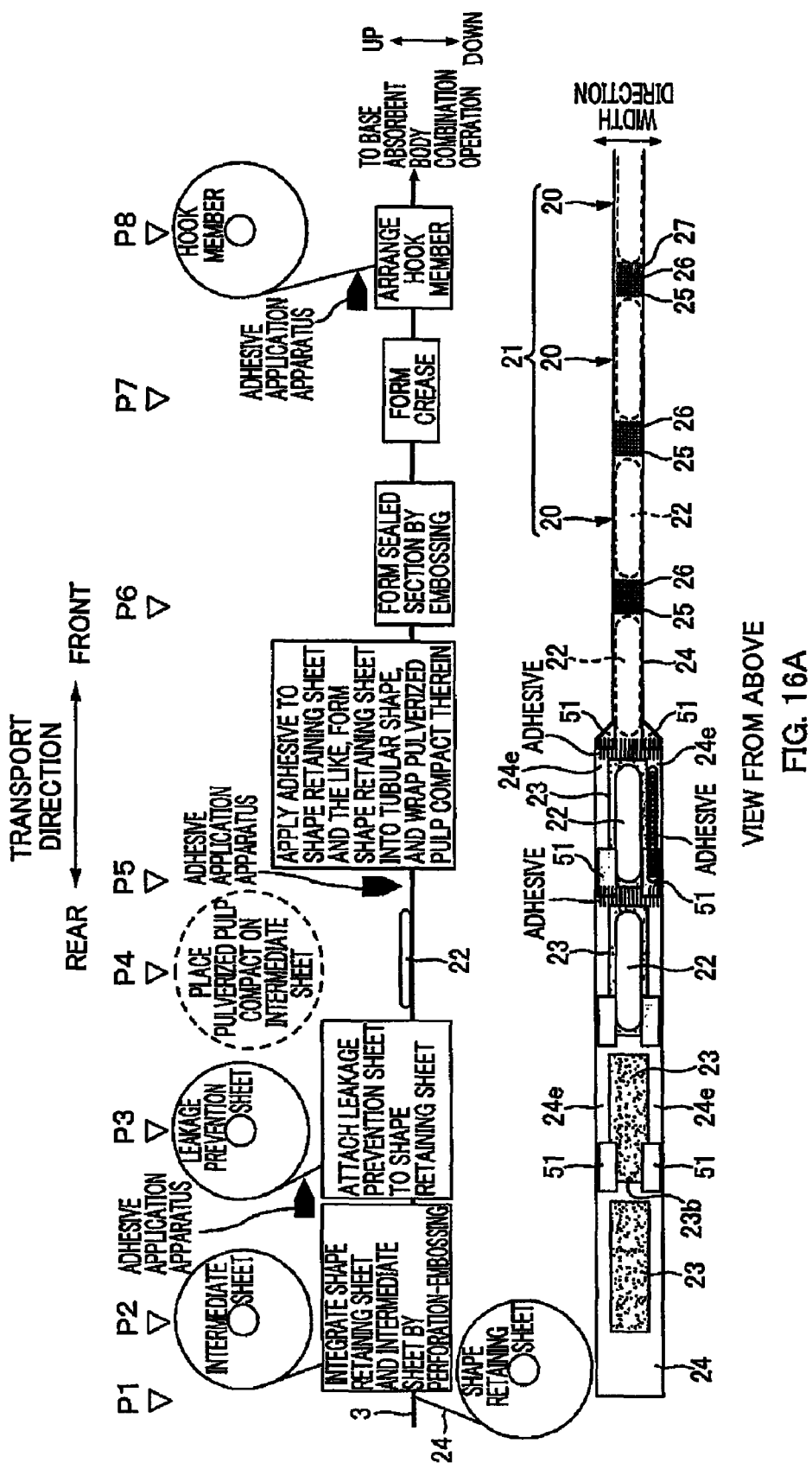
FIG. 16A is an explanatory view of a "top absorbent body production operation" in FIG. 15.

FIG. 16A is an explanatory view of the "top absorbent body production operation". FIG. 16B is an explanatory view of the "base absorbent body combination operation". In both FIG. 16A and FIG. 16B, the flow of each process is schematically shown in the upper level, and a state in which the article is being produced is shown as a plan view in the lower level. In each of the processes, while an article such as the material is transported in the transport direction by a transporting apparatus 3 or 4 such as a conveyer included in the production line, predetermined processing treatments are performed on the article at each processing position P1, P2, P3, . . . , and P12 that has been set in advance along the transport direction, and the absorbent article 1 is produced.

<Top Absorbent Body Production Operation>

First, as shown in FIG. 16A, at the first processing position P1 of the top absorbent body production operation, the belt-shaped retaining sheet 24 is reeled off a retaining sheet roll that has been wound into a roll, supplied in the form of a continuous sheet onto the transporting apparatus 3, and transported along the transport direction. In the case where the shape retaining sheet 24 is being transported by the transporting apparatus 3, air is sucked from below the transporting apparatus 3, and thus the shape retaining sheet 24 is drawn toward the transporting apparatus 3 side and stably transported.

In the following description, the downstream side and the upstream side in the transport direction are referred to as front and rear, respectively, and the direction that is perpendicular to the transport direction is referred to as a width direction. By the way, the width direction corresponds to the width direction of the absorbent article 1. Furthermore, the front and the rear in the transport direction correspond to the front and the rear in the longitudinal direction of the absorbent article 1 described above. That is to say, the front end section 1$a$ in the longitudinal direction of the absorbent article 1 is formed at the front in the transport direction, while the rear end section 1$b$ is formed at the rear in the transport direction.

At the next processing position P2, the rectangular intermediate sheet 23 that is in the form of single-cut sheet is placed on the shape retaining sheet 24 that is being transported by the transporting apparatus 3. Herein, the intermediate sheet 23 is placed in the middle in the width direction of the shape retaining sheet 24. In this state, perforation-embossing is performed on the intermediate sheet 23 and the shape retaining sheet 24, and thus the shape retaining sheet 24 and the intermediate sheet 23 are integrated.

The perforation-embossing is performed by letting a product pass through the space between two rollers (not shown) that are vertically opposed to each other. For example, one of the rollers used for the perforation-embossing is provided with conical protrusions, and the roller opposing the one roller is provided with holes into which the protrusions are inserted. The roller on which the protrusions are formed is heated. Thus, in the case where the conical protrusions pass through the shape retaining sheet 24 and the intermediate sheet 23 and openings are formed, edge sections of the openings are thermally fused, and thereby the shape retaining sheet 24 and the intermediate sheet 23 are integrated.

At the next processing position P3, the leakage prevention sheets 51 in the form of a pair of cut sheets are supplied onto the shape retaining sheet 24 with which the intermediate sheet 23 has been integrated, and are attached thereto by a hot-melt adhesive. Here, each of the leakage prevention sheets 51 is arranged at each of the end sections 24$e$ on both sides in the width direction of the shape retaining sheet 24, so that the spacing W is interposed between both leakage prevention sheets 51. As described above, the spacing W is the area with no leakage prevention sheet 51 disposed in the rear end section 20$b$ of the top absorbent body 20 shown in FIG. 13A. Furthermore, in the transport direction, each of the leakage prevention sheets 51 is disposed at a rear end section 23$b$ of the intermediate sheet 23 while spanning the rear edge of the intermediate sheet 23 in the front-and-rear direction. By the way, the processing position P3 and the processing position P2 may be arranged in the opposite order.

At the next processing position P4, the pulverized pulp 22 containing a superabsorbent polymer in a state of being shaped into a substantially rectangular parallelepiped (hereinafter, the pulverized pulp 22 in this state is also referred to as a pulverized pulp compact 22), is placed on the intermediate sheet 23. From this position, on each of the intermediate sheets 23, 23, . . . 23 disposed at intervals therebetween in the front and rear direction in the transport direction, each of the pulverized pulp compacts 22, 22, . . . 22 is placed and transported in such state.

At the next processing position P5, a hot-melt adhesive is applied to portions between each of the pulverized pulp compacts 22 that are adjacent to each other in the front-and-rear direction (portions of the leakage prevention sheets 51 and a portion of the shape retaining sheet 24), and to a portion of the shape retaining sheet 24 next to the pulverized pulp compact 22 in the width direction.

Here, the surface shape of the transporting apparatus 3 at the front in the processing position P5 is formed so that end sections on both sides in the width direction are gradually bent upward as the article is transported to the front. Thus, in the process of transporting the shape retaining sheet 24 to the front along the bent surface, the pulverized pulp compact 22 is wrapped in the shape retaining sheet 24 that has been integrated with the leakage prevention sheet 51 and the intermediate sheet 23. Note that, in this example, the side that serves as the surface of the absorbent article 1 when it is completed faces the transporting apparatus 3 side. Accordingly, in the case where the pulverized pulp compact 22 is wrapped in the shape retaining sheet 24, the end sections 24$e$ on both sides in the width direction of the shape retaining sheet 24 are overlapped and adhered to each other at upper side of the pulverized pulp compact 22, and thus the shape retaining sheet 24 is formed into a tubular-shape. At that time, the plurality of pulverized pulp compacts 22 are arranged at intervals therebetween in the front-and-rear direction in the tubular-shaped retaining sheet 24. By the way, the processing position P5 and the processing position P4 may be arranged in the opposite order.

At the next processing position P6, embossed patterns are formed by performing embossing on the portions between the pulverized pulp compacts 22 on the shape retaining sheet 24 and the like (hereinafter, referred to as embossing target portions), and thus the portions are caused to adhere. Accordingly, the shape retaining sheet 24 is sealed at the embossing target portions, and the above-described sealed sections 25 and 26 of the top absorbent body 20 are formed at the front and rear section of the pulverized pulp compact 22.

Embossing is performed by letting a product pass through the space between two rollers that are vertically opposed to each other, as in the case of the above-described perforation-embossing. More specifically, on the lower roller provided on the side of the transporting apparatus 3, protrusions are formed on a portion that abuts against the embossing target portions. The surface of the upper roller opposing the lower roller is formed flat. And here, the tips of the protrusions are formed flat, and thus concave sections with flat bottom section are formed at the embossing target portions on the shape retaining sheet 24 and the like, and the embossing target portions are compressed and sealed. The sealed portions become the sealed sections 25 and 26. As a result, the continuous body 21 of the top absorbent bodies 20 is produced in which the sealed sections 25 and 26 are formed at the front and rear of each pulverized pulp compact 22.

At the next processing position P7, a process is performed to form a crease along the thin wall section 22*f* (refer to FIG. 13A) of the pulverized pulp compact 22, in the continuous body 21 of the top absorbent bodies 20. With this processing, the absorbent article 1 is made so that it naturally bends in the middle in the width direction when it is worn on the human body. The crease is formed when the continuous body 21 of the top absorbent bodies 20 passes on a revolving plate (not shown) that is supported on a shaft along the width direction and that rotates along the transport direction. At that time, the revolving plate is configured so as to contact the thin wall section 22*f* of the pulverized pulp compact 22, via the shape retaining sheet 24.

At the next processing position P8, the hook member 27 is supplied to each top absorbent body 20. Each hook member 27 adheres to the rear sealed section 26 of each top absorbent body 20 with a hot-melt adhesive.

<Base Absorbent Body Combination Process>

As shown in FIG. 16B, in the base absorbent body combination process, each of the top absorbent bodies 20 included in the continuous body 21 of the top absorbent bodies 20 are each combined with the corresponding base absorbent bodies 10. In other words, this base absorbent body combination process corresponds to a junction of the above-mentioned top absorbent body production line on which the top absorbent body production process is performed and the base absorbent body production line. Thus, in the base absorbent body combination process, the plurality of base absorbent bodies 10, spaced away from each other at the front and rear in the transport direction, are transported from the base absorbent body production line.

More specifically, at the first processing position P9 of the base absorbent body combination process, the base absorbent body 10 is supplied from above the continuous body 21 of the top absorbent bodies 20 onto the transporting apparatus 4.

At that time, the base absorbent body 10 is positioned so that the top absorbent body 20 is in the middle in the width direction of the base absorbent body 10, and so that the front sealed section 25 of the top absorbent body 20 is positioned at the front end section 10*a* of the base absorbent body 10. Furthermore, the base absorbent body 10 is supplied so that the side of a human body abutment face, that is, the side of the surface sheet 14 is opposing the top absorbent body 20.

Note that, before supplying the base absorbent body 10, a hot-melt adhesive with a large line diameter has been applied in advance to the front sealed section 25 of each top absorbent body 20. Thus, the front sealed section 25 is lightly pressed against the base absorbent body 10, at the time the front sealed section 25 is positioned to the front end section 10*a* of the base absorbent body 10, thereby the front sealed section 25 and the base absorbent body 10 are joined to each other. The top absorbent body 20 at that time is in a form of a continuous body in which other top absorbent bodies 20 are continuously arranged at the front and rear of the top absorbent body 20. Thus, after the joining, the base absorbent bodies 10 also are transported in a continuous state.

At the next processing position P10, embossing is performed on portions in which the front and rear sealed sections 25 and 26 of the top absorbent body 20 are overlapped with the base absorbent body 10, and thus the sealed sections 25 and 26 are fixed to the base absorbent body 10. Herein, the front sealed section 25 is firmly and permanently fixed to the front end section 10*a* of the base absorbent body 10 because embossing is performed thereon in a state where the hot-melt adhesive with a large line diameter is interposed, however the rear sealed section 26 is temporarily fixed to the rear end section 10*b* of the base absorbent body 10 by an adhesive strength with a degree that allows the rear sealed section 26 to be easily separated from the base absorbent body 10 because embossing is performed thereon in a state where the hot-melt adhesive is not interposed.

At the next processing position P11, the wing sections 32 of the back face sheet 30 are bent toward the surface side, and the protection sheets 34 and 35 to which hot-melt adhesives have been applied are placed on the back face 30*c* and the wing sections 32 of the back face sheet 30. More specifically, the undergarment fixation adhesives 31 and 33 are not directly applied to the back face 30*c* of the back face sheet 30 and the wing sections 32, but applied via the protection sheets 34 and 35. And when the protection sheets 34 and 35 have been transferred to the back face 30*c* of the back face sheet 30 and the wing sections 32, and then removed therefrom, the adhesives 31 and 33 are transferred to remain on the back face 30*c* and the wing sections 32 of the back face sheet 30.

At the next processing position P12, the sealed sections 25 and 26 in the continuous body 21 of the top absorbent bodies 20 are cut with a cutter or the like to become single products, and thus the absorbent article 1 is completed. At that time, the front sealed section 25 of the top absorbent body 20 is cut so as to be substantially matched to the external outline of the base absorbent body 10. The rear sealed section 26 is cut so as to be projected rearward by approximately 20 mm from the external outline of the base absorbent body 10, and thus the pick-up section 26*a* is in a projected state.

Modified Example of the First Embodiment

Figure 17:
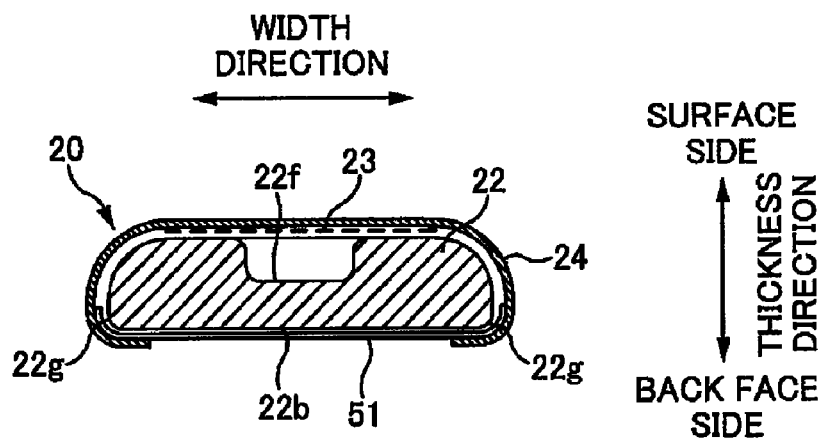
FIG. 17 is an explanatory view of a first modified example of the top absorbent body 20 according to the first embodiment.
Figure 18:
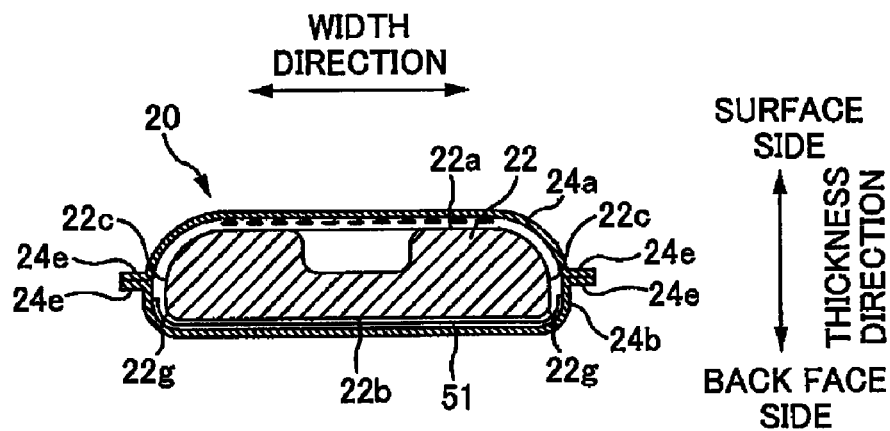
FIG. 18 is an explanatory view of a second modified example of the top absorbent body.
Figure 19:
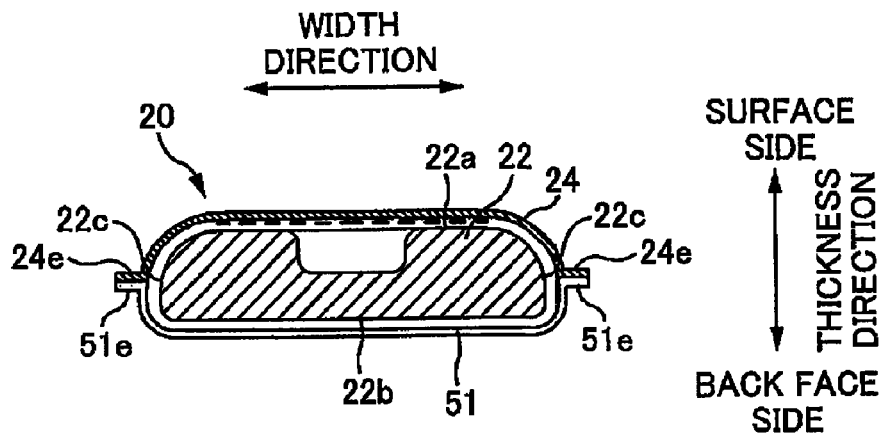
FIG. 19 is an explanatory view of a third modified example of the top absorbent body.

FIGS. 17 to 19 are all explanatory views of modified examples of the top absorbent body 20 according to the first embodiment, and are cross-sectional views of the top absorbent body 20 taken along line A-A in FIG. 12. Note that all of the modified examples in FIGS. 17 to 19 are different from the above described first embodiment, in terms of the configuration of the leakage prevention sheet 51 and the shape retaining sheet 24 of the top absorbent body 20. Hereinafter, the first to third modified examples will be described.

According to the first modified example in FIG. 17, the shape retaining sheet 24 does not cover substantially only the back face 22*b*, in the outer peripheral face of the pulverized pulp 22. The leakage prevention sheet 51 is provided so that it covers substantially only the back face 22*b* and two corner sections 22*g* on both sides thereof in the pulverized pulp 22, so as to complement the uncovered portion. More specifically, the leakage prevention sheet 51 is in an exposed state on the back face side of the top absorbent body 20, and the shape retaining sheet 24 and the leakage prevention sheet 51 cover, in a mutually complementary manner, the entire periphery of the outer peripheral face of the pulverized pulp 22. Accordingly, the first modified example is excellent costwise because the area of the shape retaining sheet 24 necessary for forming the top absorbent body 20 can be made smaller.

According to the second modified example in FIG. 18, the shape retaining sheet is constituted by two sheets, namely a shape retaining sheet 24*a* that covers the surface 22*a* side of the pulverized pulp 22, and a shape retaining sheet 24*b* that covers the back face 22*b* side of the pulverized pulp 22. The end sections 24*e* in the width direction of the sheets 24*a* and 24*b* are overlapped and joined to each other at the side faces 22*c* in the width direction of the pulverized pulp 22. Thus, the overlapped sections are projected in the form of flanges outward in the width direction. More specifically, the entire periphery of the outer peripheral face of the pulverized pulp 22 is covered by these two shape retaining sheets 24a and 24b. On the other hand, the leakage prevention sheet 51 covers substantially only the back face 22b and the two corner sections 22g on both sides thereof of the pulverized pulp 22, as in the above-mentioned first modified example in FIG. 17, and is interposed between the pulverized pulp 22 and the shape retaining sheet 24b on the side of the back face 22b.

According to the third modified example in FIG. 19, the shape retaining sheet 24 covers only the side of the surface 22a of the pulverized pulp 22, and the leakage prevention sheet 51 covers the side of the back face 22b of the pulverized pulp 22. And the end sections 24e and 51e in the width direction of the shape retaining sheet 24 and the leakage prevention sheet 51 are overlapped and joined to each other at the side faces 22c in the width direction of the pulverized pulp 22. Thus, the overlapped sections are projected in approximately the form of flanges outward in the width direction. More specifically, the shape retaining sheet 24 and the leakage prevention sheet 51 cover, in a mutually complementary manner, the entire periphery of the outer peripheral face of the pulverized pulp 22. Accordingly, the third modified example is also excellent costwise because the area of the shape retaining sheet 24 necessary for forming the top absorbent body 20 can be made smaller.

Second Embodiment

Figure 20A:
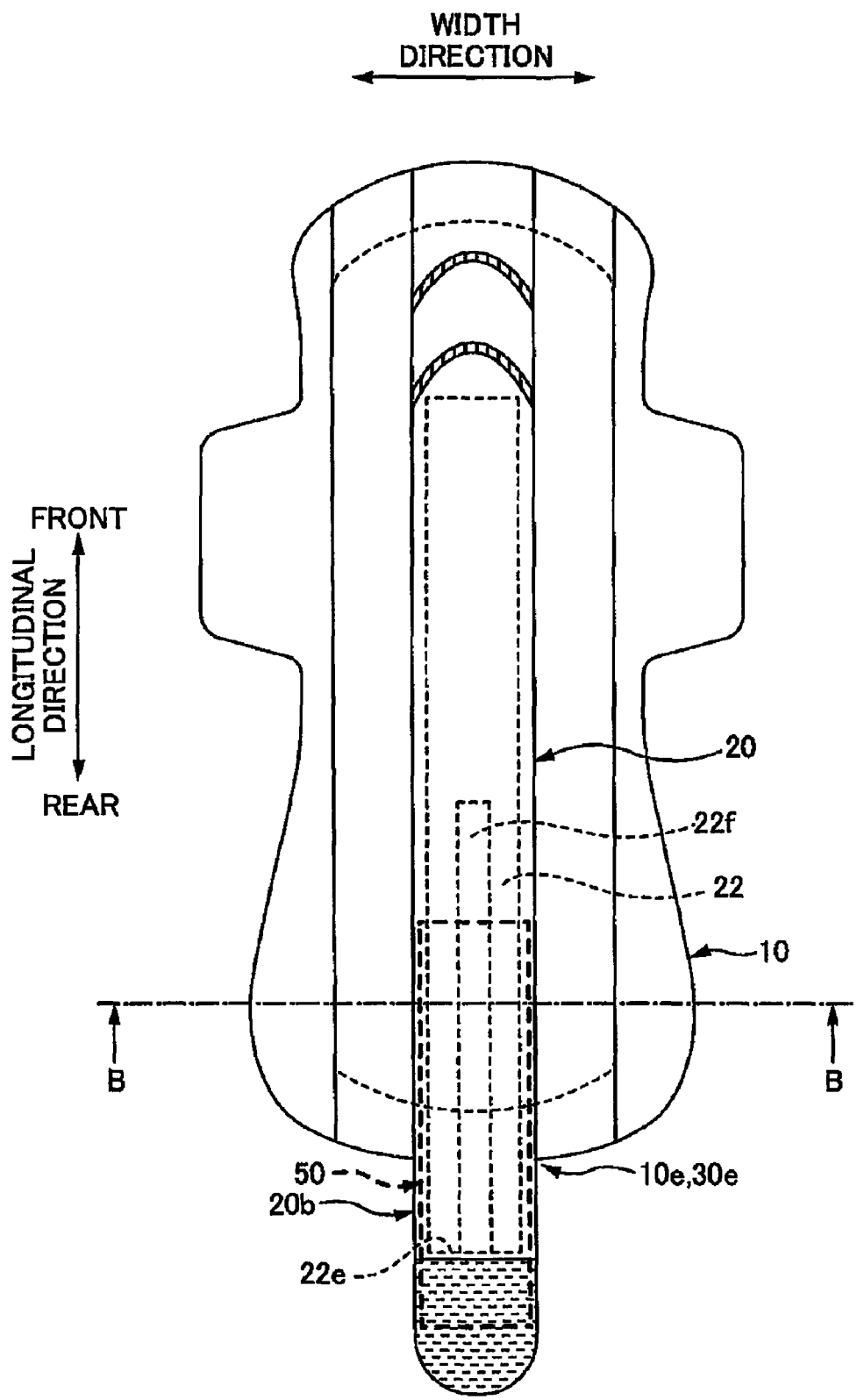
FIG. 20A is an explanatory view of the absorbent article 1 according to the second embodiment, and is a plan view of the unfolded absorbent article 1.
Figure 20B:
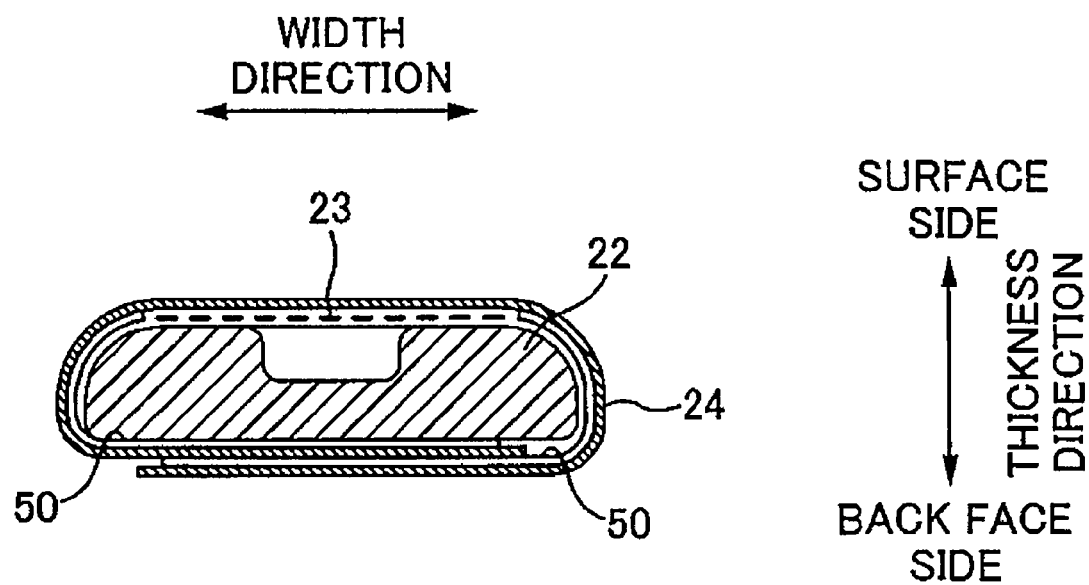
FIG. 20B is a cross-sectional view showing only the top absorbent body 20, taken along line B-B in FIG. 20A.

FIGS. 20A and 20B are explanatory views of the absorbent article 1 according to the second embodiment. FIG. 20A is a plan view of the unfolded absorbent article 1. FIG. 20B is a cross-sectional view showing only the top absorbent body 20, taken along line B-B in FIG. 20A. The absorbent article 1 of the second embodiment is different from that of the above-mentioned first embodiment, only in that the length of the top absorbent body 20 is further longer than the base absorbent body 10, and the other configurations are generally the same.

More specifically, according to the absorbent article 1 of the second embodiment, in its unfolded state (a state in which the base absorbent body 10 and the top absorbent body 20 that have been overlapped with each other are unfolded flat), the rear end section 20b of the top absorbent body 20 is significantly projected rearward from the external outline of the base absorbent body 10. More specifically, the pulverized pulp 22 in the top absorbent body 20 is extended to a position where it is projected rearward from the external outline of the base absorbent body 10. In other words, a rear edge 22e of the pulverized pulp 22 is positioned further rear than the external outline of the base absorbent body 10. In such a case, at least in the longitudinal direction, it is preferable that the fluid-impermeable layer 50 is provided throughout the following area.

More specifically, in the unfolded state of the absorbent article 1 shown in FIG. 20A, it is preferable that the fluid-impermeable layer 50 is disposed so that it is extended at least from a position of a rear edge 10e at the external outline of the base absorbent body 10 (a rear edge 30e of the back face sheet 30) to a position of the rear edge 22e of the pulverized pulp 22 of the top absorbent body 20. Further, it is more preferable that the fluid-impermeable layer 50 spans the position of the rear edge 10e at the external outline of the base absorbent body 10 (the rear edge 30e of the back face sheet 30), and at the same time, spans the position of the rear edge 22e of the pulverized pulp 22 of the top absorbent body 20. Accordingly, the undergarment 90 can be effectively prevented from getting dirty with a portion of the top absorbent body 20 projected rearward from the external outline of the base absorbent body 10.

Other Embodiments

In the description above, embodiments of the invention were described. However, the invention is not limited to these embodiments, and modifications as described below are possible.

In the foregoing embodiments, as the first embodiment, an example was described in which, in the unfolded state, only the pick-up section 26a of the top absorbent body 20 is projected from the external outline of the base absorbent body 10 (refer to FIG. 1), and as the second embodiment, an example was described in which, in the unfolded state, not only the pick-up section 26a of the top absorbent body 20 but also a section up to the position where the pulverized pulp 22 extends to in the top absorbent body 20 is projected from the external outline of the base absorbent body 10 (refer to FIG. 20A), but there is no limitation to this.

Figure 21:
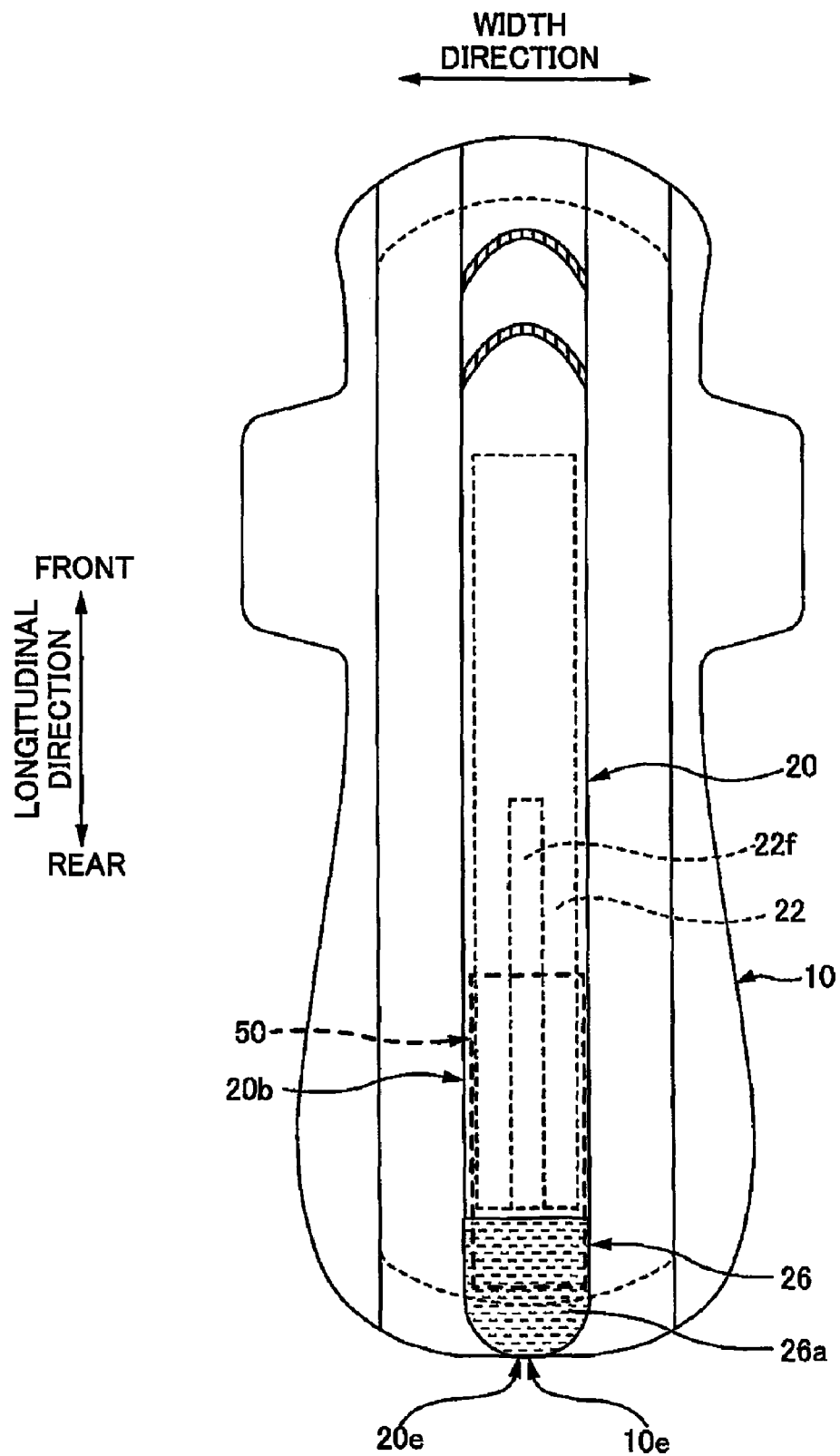
FIG. 21 is an explanatory view of the absorbent article 1 according to another embodiment, and is a plan view of the unfolded absorbent article 1.
Figure 22:
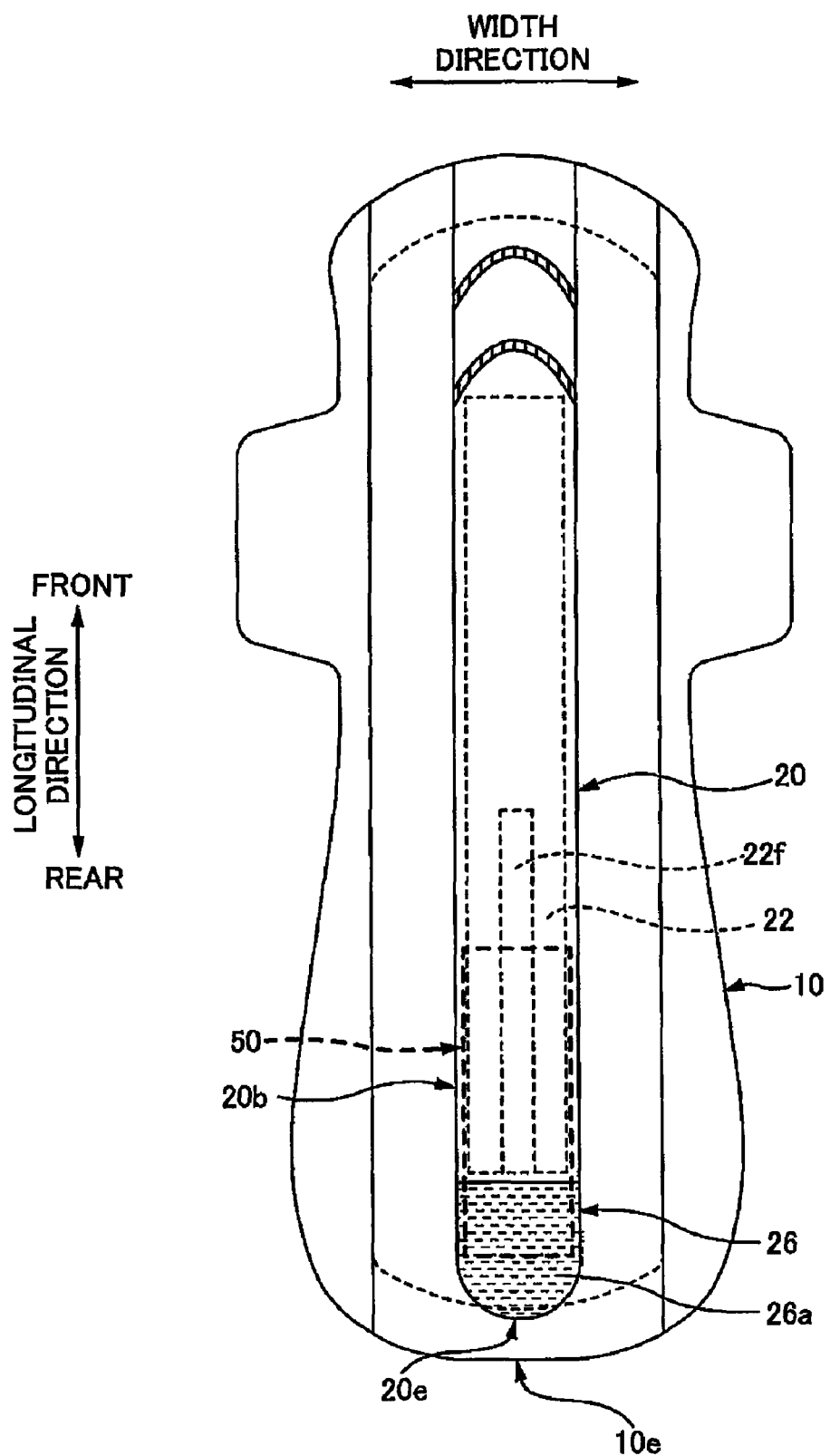
FIG. 22 is an explanatory view of the absorbent article 1 according to another embodiment, which is a plan view of the unfolded absorbent article 1.

For example, as shown in FIG. 21, a configuration is possible in which the position of the front edge of the pick-up section 26a, which is a rear edge 20e of the top absorbent body 20, is matched to the position of the rear edge 10e at the external outline of the base absorbent body 10. Alternatively, a configuration as shown in FIG. 22 is possible in which the rear edge 20e of the top absorbent body 20 is positioned forward of the rear edge 10e at the external outline of the base absorbent body 10. Note that also in these cases, it goes without saying that depending on how the top absorbent body 20 is pulled up by the user at the time it is worn, the rear end section 20b of the top absorbent body 20 may project rearward from the external outline of the base absorbent body 10.

In the foregoing embodiments, as shown in FIG. 3, a configuration was exemplified in which the base absorbent body 10 as a "main body section of the absorbent article" includes the absorbent body base material 12 constituted by, for example, the pulverized pulp 12a as a fluid-absorbent member, but there is no limitation to this. For example, the "main body section of the absorbent article" may be the above-described base absorbent body 10 excluding the absorbent body base material 12 from its configuration described above. However, in this configuration, the base absorbent body 10 does not have the pulverized pulp 12a and the like, and therefore the overall fluid-absorbing ability is poor.

In the foregoing embodiments, one absorbent body base material 12 is included in the middle in the width direction of the base absorbent body 10, but there is no limitation to this. For example, side section absorbent bodies may be included respectively along the longitudinal direction in both end sections, in the width direction of the base absorbent body 10. Moreover, instead of the side section absorbent bodies, standing gathers may be included respectively in both end sections.

In the foregoing embodiments, a sanitary napkin was described as the absorbent article 1, however, there is no limitation to this, and any product that is worn on the human body and absorbs fluid discharged from the human body is acceptable. An example includes a disposable diaper.

The invention claimed is:
1. An absorbent article adapted to be worn on a human body, and having a longitudinal direction, a width direction and a thickness direction, said absorbent article comprising:
an absorbent body having a fluid-absorbent member for absorbing fluid, and a fluid-impermeable layer, and a main body section which, on a side adapted to face the human body, in use, overlaps the absorbent body in the thickness direction, wherein the absorbent body has first and second end sections in the longitudinal direction, the first end section being fixed to the main body section, the absorbent body further has a side that is closer to the main body section than the fluid-absorbent member in the thickness direction, and a side that is adapted to be closer to the human body than the fluid-absorbent member, wherein the side closer to the main body section, in the second end section of the absorbent body, is covered with the fluid-impermeable layer, and the side adapted to be closer to the human body, in the second end section, has a portion that is not covered by the fluid-impermeable layer, the absorbent body further has a thin section in a middle part of the second end section in the width direction, said thin section being thinner than remaining sections of the second end section of the absorbent body in the width direction; and a fluid-permeable shape retaining sheet that is elongated in the longitudinal direction for retaining the fluid-absorbent member by wrapping around the fluid-absorbent member, and the fluid-impermeable layer is interposed between the fluid-absorbent member and the shape retaining sheet.

2. The absorbent article according to claim 1, wherein in an unfolded state, in which the main body section and the absorbent body overlap and are unfolded flat, the second end section of the absorbent body is projected outward from an external outline of the main body section, and in the unfolded state, the fluid-impermeable layer covers the second end section.

3. The absorbent article according to claim 1, wherein the fluid-impermeable layer is included only in the second end section and not in the first end section.

4. The absorbent article according to claim 1, wherein the fluid-impermeable layer is directly attached to the shape retaining sheet.

5. The absorbent article according to claim 1, wherein the fluid-impermeable layer is elongated in the longitudinal direction in the second end section without extending into the first end section of the absorbent body.

6. The absorbent article according to claim 1, further comprising a hook member located on the absorbent body and adapted to face away from the human body, in use, wherein the hook member does not overlap with the thin section in the thickness direction.

7. The absorbent article according to claim 2, wherein the fluid-impermeable layer has a front sealed section and a rear sealed section opposite to the front sealed section in the longitudinal direction, and in the front and rear sealed sections, the fluid-impermeable layer is folded and directly contact itself.

8. The absorbent article according to claim 1, wherein the fluid-absorbent member has a top face, a back face opposite to the top face in the thickness direction, and two side faces connecting the top face and the back face, the top face defining the side that is adapted to be closer to the human body than the fluid-absorbent member, and the fluid-impermeable layer is directly attached to the back face and the side faces without covering the top face.

9. The absorbent article according to claim 1, wherein the absorbent body further includes an intermediate sheet that has the same material as the shape retaining sheet, the intermediate sheet extends between the fluid-absorbent member and the shape retaining sheet in the longitudinal direction but does not extend to front and rear end sections of the shape retaining sheet, both said front and rear ends sections being in a folded state without including the fluid-absorbent member.

10. The absorbent article according to claim 1, wherein the fluid-absorbent member has a top face, a back face opposite to the top face in the thickness direction, and two side faces connecting the top face and the back face, the top face defining the side that is adapted to be closer to the human body than the fluid-absorbent member, the top face and the side faces are covered by the shape retaining sheet, and the back face is covered by the fluid-impermeable layer.

11. The absorbent article according to claim 1, wherein the fluid-absorbent member has a top face, a back face opposite to the top face in the thickness direction, and two side faces connecting the top face and the back face, the top face defining the side that is adapted to be closer to the human body than the fluid-absorbent member, the shape retaining sheet has an upper sheet and a lower sheet opposite to the upper sheet in the thickness direction, ends of the upper sheet directly joined to ends of the lower sheet at the side faces in the width direction, respectively, the upper sheet covers the top face of the fluid-absorbent member and the lower sheet covers the back face of the fluid-absorbent member, and the fluid-impermeable layer is sandwiched between the fluid-absorbent member and the lower sheet.

12. The absorbent article according to claim 1, wherein the fluid-absorbent member has a top face, a back face opposite to the top face in the thickness direction, and two side faces connecting the top face and the back face, the top face defining the side that is adapted to be closer to the human body than the fluid-absorbent member, the shape retaining sheet covers the top face of the fluid-absorbent member, the fluid-impermeable sheet covers the back face of the fluid-absorbent member, and ends of the shape retaining sheet are directly joined to ends of the fluid-impermeable sheet at the side faces in the width direction, respectively.

* * * * *